(12) United States Patent
Ali et al.

(10) Patent No.: US 7,411,073 B2
(45) Date of Patent: Aug. 12, 2008

(54) SELECTIVE NON-STEROIDAL GLUCOCORTICOID RECEPTOR MODULATORS

(75) Inventors: Amjad Ali, Piscataway, NJ (US); Richard Beresis, Matawan, NJ (US); Steven L. Colletti, Princeton Junction, NJ (US); Donald W. Graham, Mountainside, NJ (US); James R. Tata, Westfield, NJ (US); Christopher F. Thompson, Clark, NJ (US)

(73) Assignee: Merck & Co., Inc., Rahway, NJ (US)

( * ) Notice: Subject to any disclaimer, the term of this patent is extended or adjusted under 35 U.S.C. 154(b) by 251 days.

(21) Appl. No.: 10/544,899

(22) PCT Filed: Feb. 20, 2004

(86) PCT No.: PCT/US2004/005199

§ 371 (c)(1),
(2), (4) Date: Aug. 8, 2005

(87) PCT Pub. No.: WO2004/075840

PCT Pub. Date: Sep. 10, 2004

(65) Prior Publication Data

US 2006/0074120 A1     Apr. 6, 2006

Related U.S. Application Data

(60) Provisional application No. 60/450,811, filed on Feb. 25, 2003.

(51) Int. Cl.
C07D 231/54     (2006.01)
A01N 43/56      (2006.01)

(52) U.S. Cl. .................................. 548/359.1; 514/406
(58) Field of Classification Search ............... 548/359.1
See application file for complete search history.

(56) References Cited

U.S. PATENT DOCUMENTS

| 4,307,102 A | 12/1981 | Bell |
| 4,349,558 A | 9/1982 | Bell |
| 4,349,559 A | 9/1982 | Bell et al. |

FOREIGN PATENT DOCUMENTS

| EP | 0058841 | 12/1984 |
| WO | WO 03/086294 | 10/2003 |
| WO | WO 2004/026248 | 4/2004 |

OTHER PUBLICATIONS

Kirkemo et al, "Synthesis of Methyl 3,5,9,11,13-Pentaoxotetradecanoate, a "Skipped" Heptaketide, via Ozonolysis of a Hydroaromatic System" J. Org. Chem. 1985, 50, 1316-1319.*
Medline Encyclopedia for "polyarteritis nodosa" entry updated Aug. 22, 2006 at http://www.nlm.nih.gov/medlineplus/ency/article/001438.htm.*

* cited by examiner

*Primary Examiner*—Kamal A. Saeed
*Assistant Examiner*—Robert Havlin
(74) *Attorney, Agent, or Firm*—Curtis C. Panzer; Valerie J. Camara

(57) ABSTRACT

The present invention encompasses compounds of Formula (I) or pharmaceutically acceptable salts or hydrates thereof, which are useful as novel non-steroidal selective glucocorticoid receptor modulators for treating a variety of autoimmune and inflammatory diseases or conditions, and possess advantages over steroidal glucocorticoid ligands with respect to undesireable side-effects, efficacy, toxicity and/or metabolism. Pharmaceutical compositions and methods of use are also included.

11 Claims, No Drawings

SELECTIVE NON-STEROIDAL GLUCOCORTICOID RECEPTOR MODULATORS

CROSS REFERENCE TO RELATED APPLICATIONS

This application is a U.S. national Phase application under 35. U.S.C. §371 of PCT Application No. PCT/US2004/005199, filed Feb. 20, 2004, which claims priority under 35 U.S.C. 119 to U.S. No. 60/450,811, filed Feb. 25, 2003.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor (GR) has an essential role in regulating human physiology and immune response. Steroids that interact with the glucocorticoid receptor have been shown to be potent anti-inflammatory agents, although cross-reactivity with other steroid hormone receptors such as the mineralocorticoid, progesterone and androgen receptors can lead to problematic ancillary pharmacology.

The dissociation of transactivation from transrepression at the glucocorticoid receptor is believed to be an approach toward improving the side-effect profile related to steroid therapy. The beneficial anti-inflammatory activity of GR modulators, such as steroids, is believed to occur through the transrepression of genes encoding for proinflammatory cytokines, adhesion molecules and enzymes. Many of the undesireable side-effects associated with such agents are believed to occur through the transactivation, or induction, of gene transcription leading to the downstream perturbation of homeostatic endocrine function. Some of these affected metabolic processes include induced gluconeogenesis, induced amino acid degradation, osteoporosis, suppression of HPA axis, induction of secondary adrenal suppression, changes in electrolyte concentration, changes in lipid metabolism, growth retardation, impaired wound healing and skin thinning. Weak, partial and full agonism of GR related to transrepression and transactivation, including potential antagonism of the receptor regarding transactivation, may be applied to the treatment of inflammatory and autoimmune diseases such as rheumatoid arthritis and asthma. For recent reviews see: (a) *Recent Advances in Glucocorticoid Receptor Action*; Cato, A. C. B., Schacke, H., Asadullah, K., Eds.; Springer-Verlag: Berlin-Heidelberg, Germany, 2002. (b) Coghlan, M. J.; Elmore, S. W.; Kym, P. R.; Kort, M. E. In *Annual Reports in Medicinal Chemistry*; Doherty, A. M., Hagmann, W. K., Eds.; Academic Press: San Diego, Calif., USA, 2002; Vol. 37, Ch. 17, pp 167-176.

SUMMARY OF THE INVENTION

The present invention encompasses compounds of Formula I:

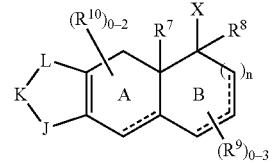

or pharmaceutically acceptable salts or hydrates thereof, which are useful as novel non-steroidal selective glucocorticoid receptor modulators for treating a variety of autoimmune and inflammatory diseases or conditions, and possess advantages over steroidal glucocorticoid ligands with respect to undesireable side-effects, efficacy, toxicity and/or metabolism. Pharmaceutical compositions and methods of use are also included.

DETAILED DESCRIPTION OF THE INVENTION

The present invention encompasses a compound represented by Formula I:

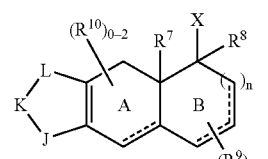

or a pharmaceutically acceptable salt or hydrate thereof, wherein:
n is 0, 1 or 2;
J is selected from $NR^1$ or $C(R^1)(R^2)$;
K is selected from $NR^3$ or $C(R^3)(R^4)$;
L is selected from $NR^5$ or $C(R^5)(R^6)$;
X is selected from the group consisting of: $-OR^a$, $-N(R^b)-Y-R^c$ or $-S(O)_j-R^d$, wherein:
Y is selected from a bond, $-(O)-$, $-C(O)-O-$, wherein the point of attachment of the "$-O-$" group is to $R^c$ forming an alkoxy moiety, $-S(O)_2-$ and $-C(O)-N(R^{12})-$, wherein the point of attachment of the nitrogen group is to $R^c$, and
j is independently 0, 1 or 2,
$R^a$, $R^b$, $R^c$, $R^d$ and $R^8$ are each independently selected from the group consisting of:
 (1) hydrogen, except that $R^d$ is not hydrogen and $R^c$ is hydrogen only when Y is a bond or $-C(O)-N(R^{12})-$,
 (2) $C_{1-6}$alkyl,
 (3) $C_{2-6}$alkenyl,
 (4) $C_{2-6}$alkynyl,
 (5) $C_{3-6}$cycloalkyl,
 (6) aryl,
 (7) aralkyl,
 (8) $HET^1$,
 (9) $-C_{1-6}$alkyl-$HET^2$,
 (10) aralkenyl,
 (11) aralkynyl and
 (12) arylsulfonylalkyl,
wherein items (2) to (5) above and the alkyl portions of items (7), (9) and (12) above and the alkenyl portion of item (10) above and the alkynyl portion of item (11) above are optionally substituted from one up to the maximum number of substitutable positions with a substituent independently selected from the group consisting of: halo, oxo, $OR^{11}$, $N(R^{12})_2$, $C_{3-6}$cycloalkyl and $C_{1-4}$alkyl-S(O)$_m$—, wherein m is 0, 1 or 2, and wherein items (6) and (8) above and the aryl portion of items (7), (10), (11) and (12) above and the $HET^2$ portion of item (9) above are optionally substituted from one up to the maximum number of substitutable positions with a substituent independently selected from the group consisting of:
  (a) halo,
  (b) $OR^{11}$,
  (c) $N(R^{12})_2$,
  (d) $C_{1-6}$alkyl,
  (e) $C_{2-6}$alkenyl,
  (f) $C_{2-6}$akynyl,
  (g) $C_{1-6}$alkyl-S(O)$_p$—, wherein p is 0, 1 or 2,
  (h) aryl,
  (i) aryl-S(O)$_q$—, wherein q is 0, 1 or 2,
  (j) $HET^3$,
  (k) aralkyl,
  (l) aroyl,
  (m) aryloxy,
  (n) aralkoxy and
  (o) CN, wherein items (d) to (g) above and the alkyl portions of item (k) above are optionally substituted from one up to the maximum number of substitutable positions with a substituent independently selected from the group consisting of: halo, $OR^{11}$ and $N(R^{12})_2$, and wherein items (h), (i), (j), (l) and (m) above and the aryl portions of items (k) and (n) above are optionally substituted from one up to the maximum number of substitutable positions with a substituent independently selected from the group consisting of: halo, $OR^{12}$ and $C_{1-4}$alkyl, $R^1$, $R^2$, $R^3$, $R^4$, $R^5$ and $R^6$ are each independently selected from the group consisting of:
  (1) hydrogen,
  (2) halo,
  (3) $C_{1-6}$alkyl,
  (4) $C_{2-6}$alkenyl,
  (5) $C_{2-6}$akynyl,
  (6) $C_{3-6}$cycloalkyl,
  (7) $C_{1-6}$alkoxy,
  (8) $C_{1-6}$alkyl-S(O)$_r$, wherein r is 0, 1 or 2,
  (9) aryl,
  (10) aralkyl,
  (11) $HET^4$ and
  (12) —$C_{1-6}$alkyl-$HET_5$, wherein items (3) to (8) above and the alkyl portions of items (10) and (12) above are optionally substituted from one up to the maximum number of substitutable positions with a substituent independently selected from the group consisting of: halo, $OR^{11}$, $N(R^{12})_2$ and $C_{1-6}$alkyl-S(O)$_2$—, wherein s is 0, 1 or 2; and wherein items (9) and (11) and the aryl portion of items (10) and the HET portion of item (12) are optionally substituted from one up to the maximum number of substituable positions with a substituent independently selected from the group consisting of:
  (a) halo,
  (b) $OR^{11}$,
  (c) $N(R^{12})_2$,
  (d) $C_{1-6}$alkyl,
  (e) $C_{2-6}$alkenyl,
  (f) $C_{2-6}$akynyl and
  (g) $C_{1-6}$alkyl-S(O)$_t$—, wherein t is 0, 1 or 2, wherein items (d) to (g) above are optionally substituted with from one up to the maximum number of substitutable positions with a substituent independently selected from the group consisting of: halo, $OR^1$ 1 and $N(R^{12})_2$, or $R^1$ and $R^3$ or $R^3$ and $R^5$ may be joined together to form a double bond;

$R^7$ is selected from the group consisting of:
  (1) hydrogen,
  (2) $OR^{11}$,
  (3) $C_{1-4}$alkyl,
  (4) aryl and
  (5) aralkyl, wherein item (3) above and the alkyl portion of item (5) above are optionally substituted with from one up to the maximum number of substitutable positions with a substituent independently selected from the group consisting of: halo, $OR^1$ 1 and $N(R^{12})_2$, and wherein item (4) above and the aryl portion of item (5) above are optionally substituted with from one up to the maximum number of substitutable positions with a substituent independently selected from the group consisting of:
  (a) halo,
  (b) $OR^{11}$,
  (c) $N(R^{12})_2$,
  (d) $C_{1-6}$alkyl,
  (e) $C_{2-6}$alkenyl and
  (f) $C_{2-6}$akynyl, wherein items (d) to (f) above are optionally substituted with from one up to the maximum number of substitutable positions with a substituent independently selected from the group consisting of: halo, $OR^{11}$ and $N(R^{12})_2$;

each $R^9$ and $R^{10}$ is independently selected from the group consisting of:
  (1) halo,
  (2) $C_{1-6}$alkyl,
  (3) $C_{2-6}$alkenyl,
  (4) $C_{1-6}$alkoxy and
  (5) hydroxy, wherein items (2) to (4) above are optionally substituted from one up to the maximum number of substitutable positions with a substituent independently selected from the group consisting of: halo, $OR^{12}$, $N(R^{11})_2$ and $C_{1-6}$alkyl-S(O)$_u$—, wherein u is 0, 1 or 2;

each $R^{11}$ and $R^{12}$ is independently selected from the group consisting of hydrogen and $C_{1-4}$alkyl, optionally substituted from one up to the maximum number of substitutable positions with halo; and $HET^1$, $HET^2$, $HET^3$, $HET^4$ and $HET^5$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The optional double bond shown in ring A of the compound of Formula I is depicted as a dotted line and means that the double bond may or may not be present as shown below:

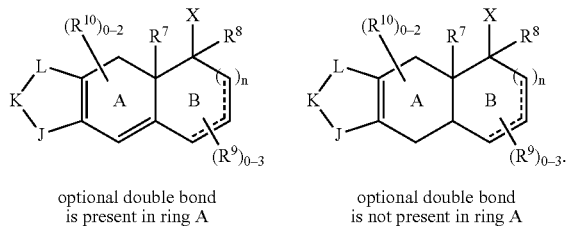

optional double bond is present in ring A optional double bond is not present in ring A The substituent $R^{10}$ in Formula I may or may not be present. When present, one or two $R^{10}$ groups may occupy the following positions:

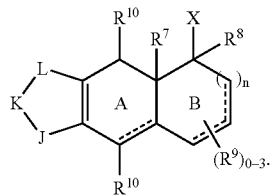

Two $R^{10}$ groups may reside on the same carbon atom.

The substituent $R^9$ in Formula I may or may not be present. When present, one, two or three $R^9$ groups may occupy the following positions:

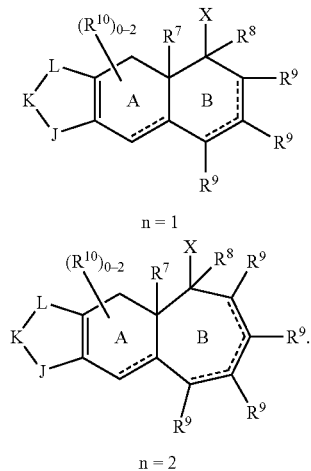

Two $R^9$ groups may reside on the same carbon atom.

The optional double bonds show in ring B of the compound of Formula I may occupy the following positions:

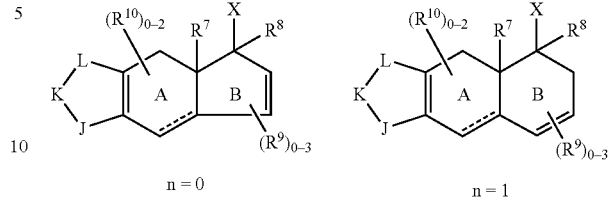

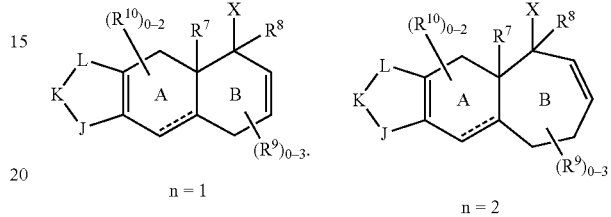

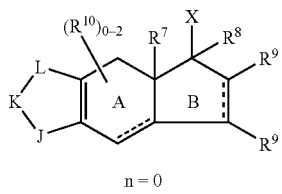

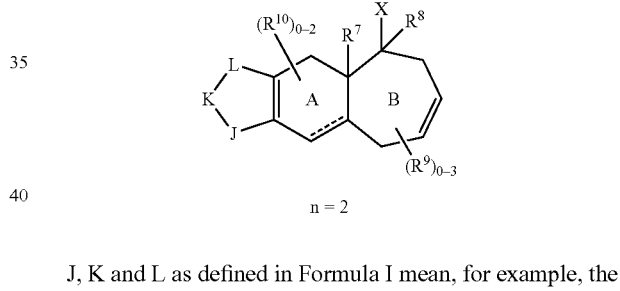

J, K and L as defined in Formula I mean, for example, the following structures:

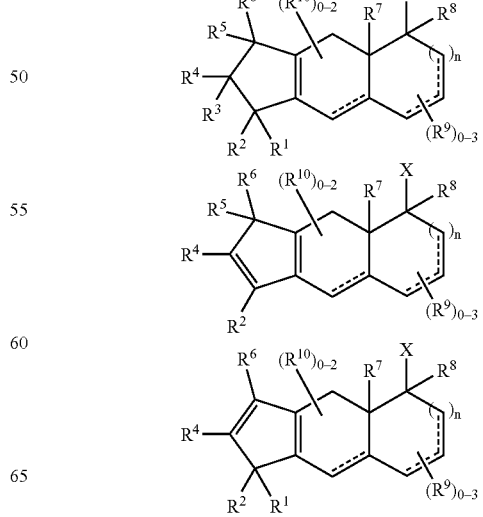

-continued
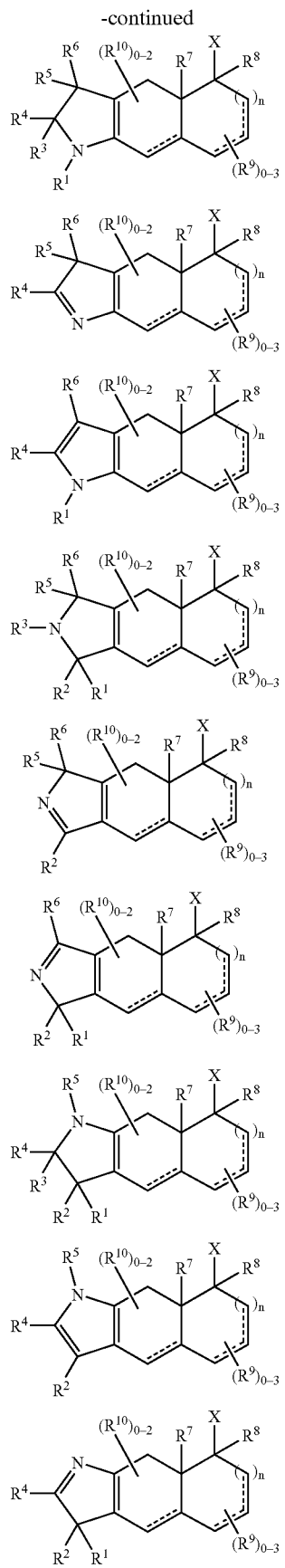
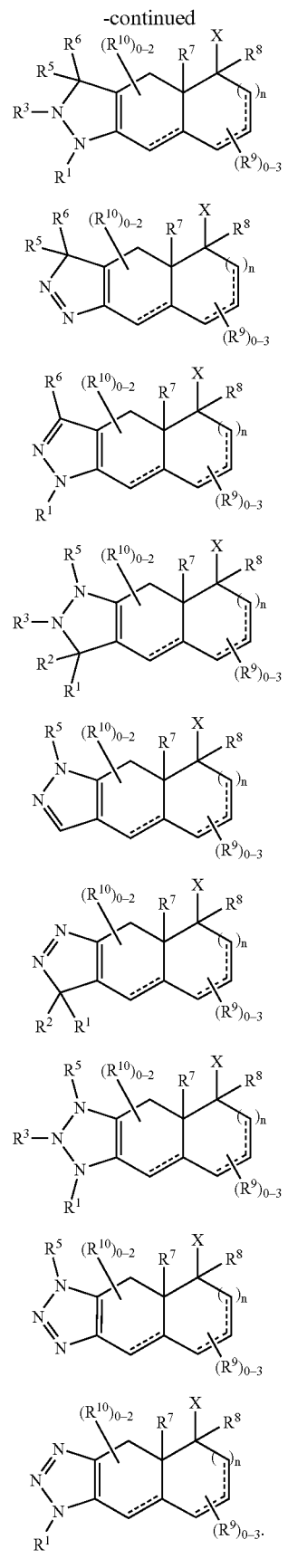

An embodiment of the invention encompasses a compound of Formula I wherein:
J is NR$^1$;
K is NR$^3$;
L is C(R$^5$)(R$^6$); and
R$^3$ and R$^5$ are joined together to form a double bond.

Another embodiment of the invention encompasses a compound of Formula I wherein the optional double bond shown in ring A of the compound of Formula I is present.

Another embodiment of the invention encompasses a compound of Formula I wherein X is —OR$^a$.

Another embodiment of the invention encompasses a compound of Formula I wherein X is —N(R$^b$)—Y—R$^c$, wherein Y is selected from —C(O)—, —C(O)—O—, wherein the point of attachment of the "—O—" group is to R$^c$ forming an alkoxy moiety, —S(O)$_2$— and —C(O)—N(R$^{12}$)—, wherein the point of attachment of the nitrogen group is to R$^c$.

Another embodiment of the invention encompasses a compound of Formula I wherein X is —S(O)$_j$-R$^d$.

Another embodiment of the invention encompasses a compound of Formula I wherein n is 0 and the optional double bonds shown in ring B are not present.

An embodiment of the invention encompasses a compound of Formula II:

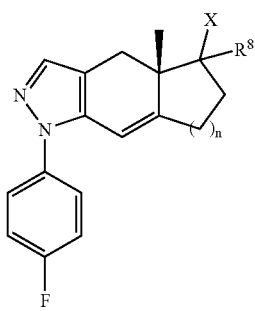

II or a pharmaceutically acceptable salt or hydrate thereof, wherein:
X is selected from the group consisting of: —OR$^a$, —N(R$^b$)—Y—R$^c$, —S(O)$_j$-R$^d$, wherein:
Y is selected from a bond, —C(O)—, —C(O)—O—, wherein the point of attachment of the "—O—" group is to R$^c$ forming an alkoxy moiety, —S(O)$_2$— and —C(O)—N(R$^{12}$)—, wherein the point of attachment of the nitrogen group is to R$^c$, and
j is 0, 1 or 2,
n is 1 or 2,
R$^a$, R$^b$, R$^c$, R$^d$ and R$^8$ are each independently selected from the group consisting of:
  (1) hydrogen, except that R$^d$ is not hydrogen and R$^c$ is hydrogen only when Y is a bond or —C(O)—N(R$^{12}$)—,
  (2) C$_{1-6}$alkyl,
  (3) C$_{2-6}$alkenyl,
  (4) C$_{2-6}$akynyl,
  (5) C$_{3-6}$cycloalkyl,
  (6) aryl,
  (7) aralkyl,
  (8) HET$_1$,
  (9) —C$_{1-6}$alkyl-HET$^2$,
  (10) aralkenyl,
  (11) aralkynyl and
  (12) arylsulfonylalkyl,
wherein items (2) to (5) above and the alkyl portions of items (7), (9) and (12) above and the alkenyl portion of item (10) above and the alkynyl portion of item (11) above are optionally substituted with oxo and optionally substituted with one to three substituents independently selected from the group consisting of: halo, OR$^{11}$, N(R$^{12}$)$_2$, C$_{3-6}$cycloalkyl and C$_{1-4}$alkyl-S(O)$_m$—, wherein m is 0, 1 or 2, and
wherein items (6) and (8) above and the aryl portion of items (7), (10), (11) and (12) above and the HET$^2$ portion of item (9) above are optionally substituted with one to five substituents independently selected from the group consisting of:
  (a) halo,
  (b) OR$^{11}$,
  (c) N(R$^{12}$)$_2$,
  (d) C$_{1-6}$alkyl,
  (e) C$_{2-6}$alkenyl,
  (f) C$_{2-6}$akynyl,
  (g) C$_{1-6}$alkyl-S(O)$_p$—, wherein p is 0, 1 or 2,
  (h) aryl,
  (i) aryl-S(O)$_q$—, wherein q is 0, 1 or 2,
  (j) HET$^3$,
  (k) aralkyl,
  (l) aroyl,
  (m) aryloxy,
  (n) aralkoxy and
  (o) CN,
wherein items (d) to (g) above and the alkyl portions of item (k) above are optionally substituted with one to three substituents independently selected from the group consisting of: halo, OR$^{11}$ and N(R$^{12}$)$_2$, and
wherein items (h), (i), (j), (l) and (m) above and the aryl portions of items (k) and (n) above are optionally substituted with one to three substituents independently selected from the group consisting of: halo, OR$^{12}$ and C$_{1-4}$alkyl,
each R$^{11}$ and R$^{12}$ is independently selected from the group consisting of hydrogen and C$_{1-4}$alkyl, optionally substituted with 1 to 3 halo groups; and
HET$^1$, HET$^2$ and HET$^3$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Another embodiment of the invention encompasses a compound of Formula II wherein
X is —OR$^a$
n is 1, and
R$^a$ is selected from the group consisting of:
  (1) hydrogen,
  (2) acetyl, (3) benzyl,
(4) $C_{1-6}$alkyl,
(5) $C_{2-6}$alkenyl,
(6) $C_{2-6}$alkynyl and
(7) $C_{3-6}$cycloalkyl, $R^8$ is selected from the group consisting of:
(1) hydrogen,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) $HET^1$,
(9) —$C_{1-6}$alkyl-$HET^2$,
(10) aralkenyl,
(11) aralkynyl, and
(12) arylsulfonylalkyl wherein items (2) to (5) above and the alkyl portions of items (7), (9) and (12) above and the alkenyl portion of item (10) above and the alkynyl portion of item (11) above are optionally substituted with oxo and optionally substituted with one to three substituents independently selected from the group consisting of: halo, $OR^{11}$ and $C_{3-6}$cycloalkyl, wherein items (6) and (8) above and aryl portion of items (7), (10), (11) and (12) above and the $HET^2$ portion of item (9) above are optionally substituted with one to five substituents independently selected from the group consisting of:
(a) halo,
(b) $C_{1-6}$alkyl,
(c) $C_{1-4}$alkoxy and
(d) aryl, $R^{11}$ is selected from the group consisting of hydrogen and $C_{1-4}$alkyl, optionally substituted with 1 to 3 halo groups; and $HET^1$ and $HET^2$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Within this embodiment is encompassed a compound of Formula II wherein:

$R^8$ is selected from the group consisting of:
(1) hydrogen,
(2) $C_{1-6}$alkyl,
(3) $C_{2-6}$alkenyl,
(4) $C_{2-6}$akynyl,
(5) $C_{3-6}$cycloalkyl,
(6) phenyl or naphthyl,
(7) benzyl or phenethyl,
(8) benzothiophene,
(9) phenylethenyl,
(10) phenylethynyl, and
(11) phenylsulfonylmethyl, wherein items (2) to (5) above are optionally substituted with one to three substituents independently selected from the group consisting of: halo, $OR^{11}$ and $C_{3-6}$cycloalkyl, wherein item (6) above and the phenyl portions of items (7), (9), (10) and (11) above are optionally substituted with one to five substituents independently selected from the group consisting of:
(a) halo,
(b) $C_{1-6}$alkyl,
(c) $C_{1-4}$alkoxy and
(d) phenyl.

Another embodiment of the invention encompasses a compound of Formula II wherein:

X is —$N(R^b)$—Y—$R^c$, wherein:

Y is selected from —C(O)—, —C(O)—O—, wherein the point of attachment of the "—O—" group is to $R^c$ forming an alkoxy moiety, —$S(O)_2$— and —C(O)—$N(R^{12})$—, wherein the point of attachment of the nitrogen group is to $R^c$, and n is 1, $R^8$ is hydrogen, and $R^b$ and $R^c$ are each independently selected from the group consisting of:
(1) hydrogen, except that $R^c$ is not hydrogen,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) $HET^1$,
(9) —$C_{1-6}$alkyl-$HET^2$,
(10) aralkenyl,
(11) aralkynyl and
(12) arylsulfonylalkyl, wherein items (2) to (5) above and the alkyl portions of items (7), (9) and (12) above and the alkenyl portion of item (10) above and the alkynyl portion of item (11) above are optionally substituted with oxo and optionally substituted with with one to three substituents independently selected from the group consisting of: halo, $OR^{11}$, $N(R^{12})_2$, $C_{3-6}$cycloalkyl and $C_{1-4}$alkyl-$S(O)_m$—, wherein m is 0, 1 or 2, and wherein items (6) and (8) above and the aryl portion of items (7), (10), (11) and (12) above and the $HET^2$ portion of item (9) above are optionally substituted with one to five substituents independently selected from the group consisting of:
(a) halo,
(b) $OR^{11}$,
(c) $N(R^{12})_2$,
(d) $C_{1-6}$alkyl,
(e) $C_{2-6}$alkenyl,
(f) $C_{2-6}$akynyl,
(g) $C_{1-6}$alkyl-$S(O)_p$—, wherein p is 0, 1 or 2,
(h) aryl,
(i) aryl-$S(O)_q$—, wherein q is 0, 1 or 2,
(j) $HET^3$,
(k) aralkyl,
(l) aroyl,
(m) aryloxy,
(n) aralkoxy and
(o) CN, wherein items (d) to (g) above and the alkyl portions of item (k) above are optionally substituted with one to three substituents independently selected from the group consisting of: halo, $OR^{11}$ and $N(R^{12})_2$, and wherein items (h), (i), (j), (l) and (m) above and the aryl portions of items (k) and (n) above are optionally substituted with one to three substituents independently selected from the group consisting of: halo, $OR^{12}$ and $C_{1-4}$alkyl, each $R^{11}$ and $R^{12}$ is independently selected from the group consisting of hydrogen and $C_{1-4}$alkyl, optionally substituted with 1 to 3 halo groups; and $HET^1$, $HET^2$ and $HET^3$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Within this embodiment is encompassed a compound of Formula II wherein:

$R^b$ and $R^c$ are each independently selected from the group consisting of:
(1) hydrogen, except that $R^c$ is hydrogen only when Y is a bond or —C(O)—N($R^{12}$)—,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) $HET^1$,
(9) —$C_{1-6}$alkyl-$HET^2$,
(10) aralkenyl, and
(11) aralkynyl, wherein items (2) to (5) above are optionally substituted with 1-3 halo groups, and wherein items (6) and (8) and aryl portion of items (7), (10) and (11) above and the $HET^2$ portion of item (9) above are optionally substituted with one to five substituents independently selected from the group consisting of:
(a) halo,
(b) $C_{1-4}$alkyl, optionally substituted with 1-3 halo groups, and
(c) $C_{1-4}$alkylthio, $HET^1$ and $HET^2$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Also within this embodiment is encompassed a compound of Formula II wherein:

$R^b$ is selected from the group consisting of: hydrogen and $C_{1-4}$alkyl, and $R^c$ is selected from the group consisting of:
(1) $C_{1-4}$alkyl,
(2) phenyl or benzyl, each optionally substituted with 1 to 5 groups independently selected from fluoro, chloro and trifluoromethyl,
(3) naphthyl,
(4) thiopheneyl,
(5) pyridyl,
(6) isoquinolyl,
(7) pyrimidyl and
(8) pyrazyl, wherein items (4) to (8) above are optionally substitited with 1 to 5 groups independently selected from fluoro, chloro, methyl, methylthio and trifluoromethyl.

Also within this embodiment of the invention is encompassed a compound of Formula II wherein $R^c$ is phenyl, optionally substituted with 1 to 5 groups independently selected from fluoro, chloro and trifluoromethyl.

Another embodiment of the invention encompasses a compound of Formula II wherein:

X is —S(O)$_j$-$R^d$, wherein j is 0, 1 or 2,
n is 1,
$R^8$ is hydrogen, and
$R^d$ is selected from the group consisting of:
(1) $C_{1-6}$alkyl,
(2) $C_{2-6}$alkenyl,
(3) $C_{2-6}$akynyl,
(4) $C_{3-6}$cycloalkyl,
(5) aryl,
(6) aralkyl,
(7) $HET^1$,
(8) —$C_{1-6}$alkyl-$HET^2$,
(9) aralkenyl, and
(10) aralkynyl, wherein items (1) to (4) above are optionally substituted with 1-3 halo groups, and wherein items (5) and (7) and aryl portion of items (6), (9) and (10) above and the $HET^2$ portion of item (8) above are optionally substituted with one to five substituents independently selected from the group consisting of:
(a) halo,
(b) $C_{1-4}$alkyl, optionally substituted with 1-3 halo groups, and
(c) $C_{1-4}$alkylthio, and $HET^1$ and $HET^2$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

Within this embodiment is encompassed a compound of Formula II wherein $R^d$ is phenyl, optionally substituted with 1 to 5 groups independently selected from fluoro, chloro and trifluoromethyl.

Another embodiment of the invention encompasses a pharmaceutical composition comprising a compound of Formula I in combination with a pharmaceutically acceptable carrier.

Another embodiment of the invention encompasses a method for treating a glucocorticoid receptor mediated disease or condition in a mammalian patient in need of such treatment comprising administering the patient a compound of Formula I in an amount that is effective for treating the glucocorticoid receptor mediated disease or condition.

Within this embodiment is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hyperglycemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another embodiment of the invention encompasses a method of selectively modulating the transactivation, transrepression, agonism and antagonism effects of the glucocorticoid receptor in a mammal comprising administering to the mammal a compound of Formula I in an amount that is effective to modulate the glucocorticoid receptor.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aralkenyl" means an alkenyl group as defined above of 2 to 6 carbon atoms with an aryl group as defined above substituted for one of the alkenyl hydrogen atoms, for example, phenethenyl and the like.

The term "aralkynyl" means an alkynyl group as defined above of 2 to 6 carbon atoms with an aryl group as defined above substituted for one of the alkynyl hydrogen atoms, for example, phenethynyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

For all of the above definitions, each reference to a group is independent of all other references to the same group when referred to in the Specification. For example, if both $R^1$ and $R^2$ are aryl, the definitions of aryl are independent of each other and $R^1$ and $R^2$ may be different aryl groups, for example phenyl and naphthyl.

The term "arylsulfonylalkyl" means aryl as defined above linked to a sulfonyl group linked to an alkyl group as defined above of 1 to 6 carbon atoms, such as phenylsulfonylmethyl and the like.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
9-BBN=9-borabicyclo[3.3.1]nonane
BOP=benzotriazol-1-yloxy-tris(dimethylamino)-phosphonium hexafluorophosphate
Dess-Martin periodinane=[1,1,1-tris(acetyloxy)-1,1-dihydro-1,2-benziodoxol-3-(1H)-one]
dba=dibenzylideneacetone
DIEA=diisopropylethylamine (Hunig's base)
DMAC=N,N-dimethylacetamide
DMAP=4-(dimethylamino)pyridine
DME=ethylene glycol dimethylether
DMF=N,N-dimethylformamide
DMSO=dimethyl sulfoxide
dppf=1,1'-bis(diphenylphosphino)ferrocene
E=transoid
HMPA=hexamethylphosphoramide
HOBt=1-hydroxybenzotriazole
HPLC=high performance liquid chromatography
LCMS=tandem HPLC followed by MS
MS=mass spectrum (or mass spectroscopy)
MsCl=methanesulfonyl chloride
N=nitrogen-substituted
NBS=N-bromosuccinimide
NMR=nuclear magnetic resonance
NSAID=non-steroidal anti-inflammatory drug
TFA=trifluoroacetic acid
THF=tetrahydrofuran
TLC=thin layer chromatography
z=cisoid Alkyl Group Abbreviations
n=normal
Me=methyl
Et=ethyl
n-Pr=normal propyl
i-Pr=isopropyl
n-Bu=normal butyl
i-Bu=isobutyl
s-Bu=secondary butyl
t-Bu=(tert) or tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, paratoluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg. The "effective amount" for treatment refers to an optimal amount of drug or pharmaceutical agent which elicits the greatest index between desireable pharmacology and undesireable side-effects.

For the treatment of glucocorticoid receptor mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of Formula I to selectively modulate glucocorticoid receptors makes them useful for treating, preventing or reversing the progression of a variety of inflammatory and autoimmune diseases and conditions. Thus, the compounds of the present invention are useful to treat, prevent or ameliorate the following diseases or conditions: inflammation, tissue rejection, auto-immunity, various malianancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity and metabolic syndrome.

The compounds of the present invention are also useful for treating, preventing or reversing the progression of disease states involving systemic inflammation such as inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pernphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitus, erythema nodosum, acne, hirsutism, toxic epidermal necrolysis, erythema multiform, cutaneous T-cell lymphoma.

The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IIL-I expression, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

The invention also encompasses a method for treating a glucocorticoid receptor mediated disease comprising concomitantly administering to a patient in need of such treatment a compound of Formula I and one or additional more agents. For treating or preventing asthma or chronic obstructive pulmonary disease, the compounds of Formula I may be combined with one or more agents selected from the group consisting of: θ-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formula I may be combined with one or the following: a salicylate, including acetylsalicylic acid, a non-steroidal antiinflammatory drug, including indomethacin, sulindac, mefenamic, meclofenamic, tolfenamic, tolmetin, ketorolac, dicofenac, ibuprofen, naproxen, fenoprofen, ketoprofen, flurbiprofin and oxaprozin, a TNF inhibitor, including etanercept and infliximab, an IL-1 receptor antagonist, including anakinra, a cytotoxic or immunosuppressive drug, including methotrexate, leflunomide, azathioprine and cyclosporine, a gold compound, hydroxychloroquine or sulfasalazine, penicillamine, darbufelone, and a p38 kinase inhibitor. The compound of Formula I may also be used in combination with bisphonates such as alendronate to treat a glucocorticoid mediated disease and simultaneously inhibit osteoclast-mediated bone resorption.

Methods of Synthesis

The compounds of the invention are prepared by the following reaction schemes. All substituents are as defined above unless indicated otherwise.

Scheme 1
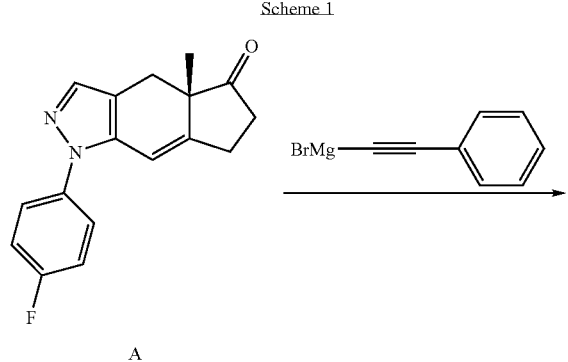
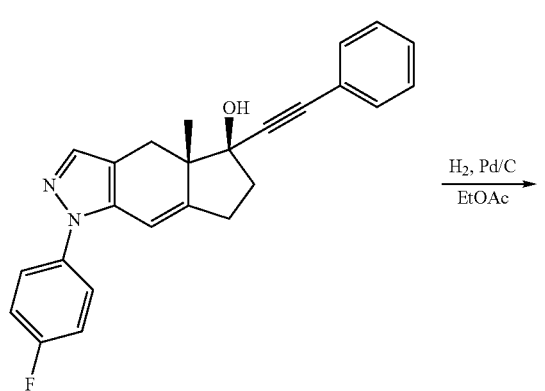
Scheme 2
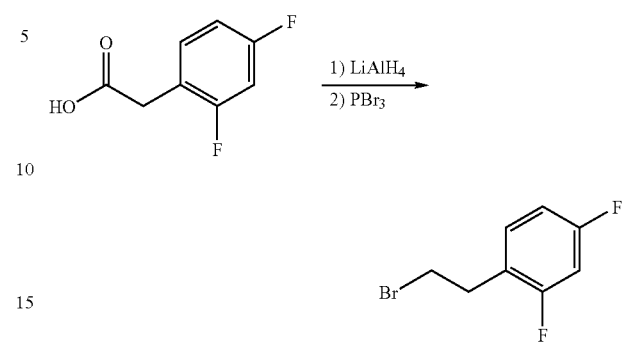
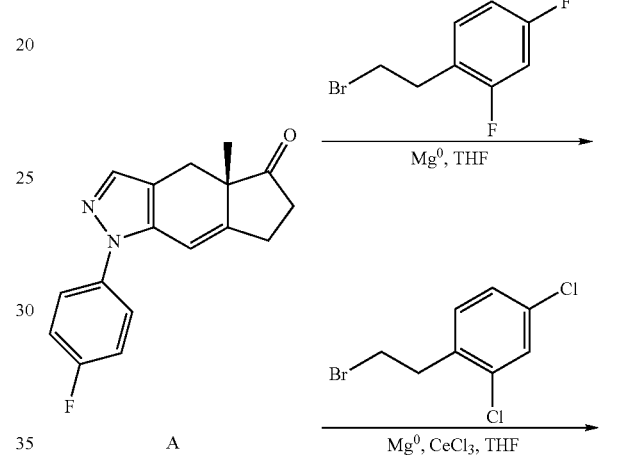
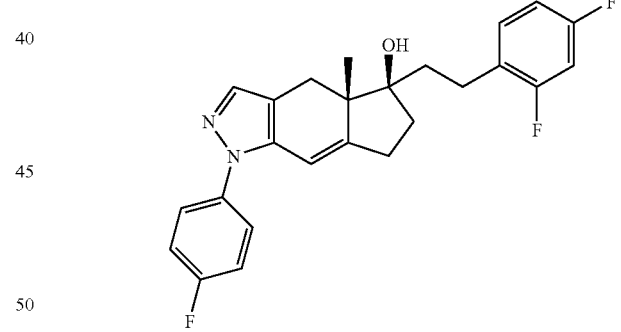
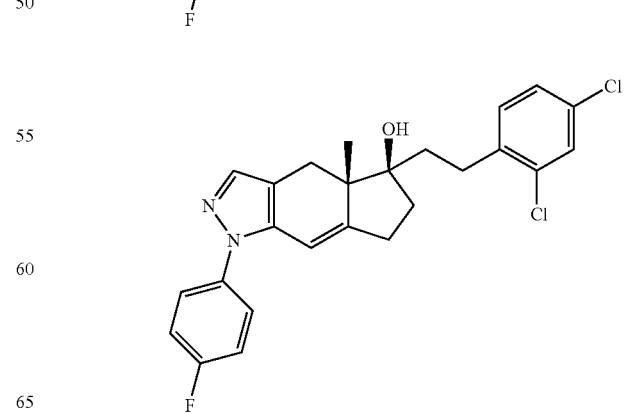

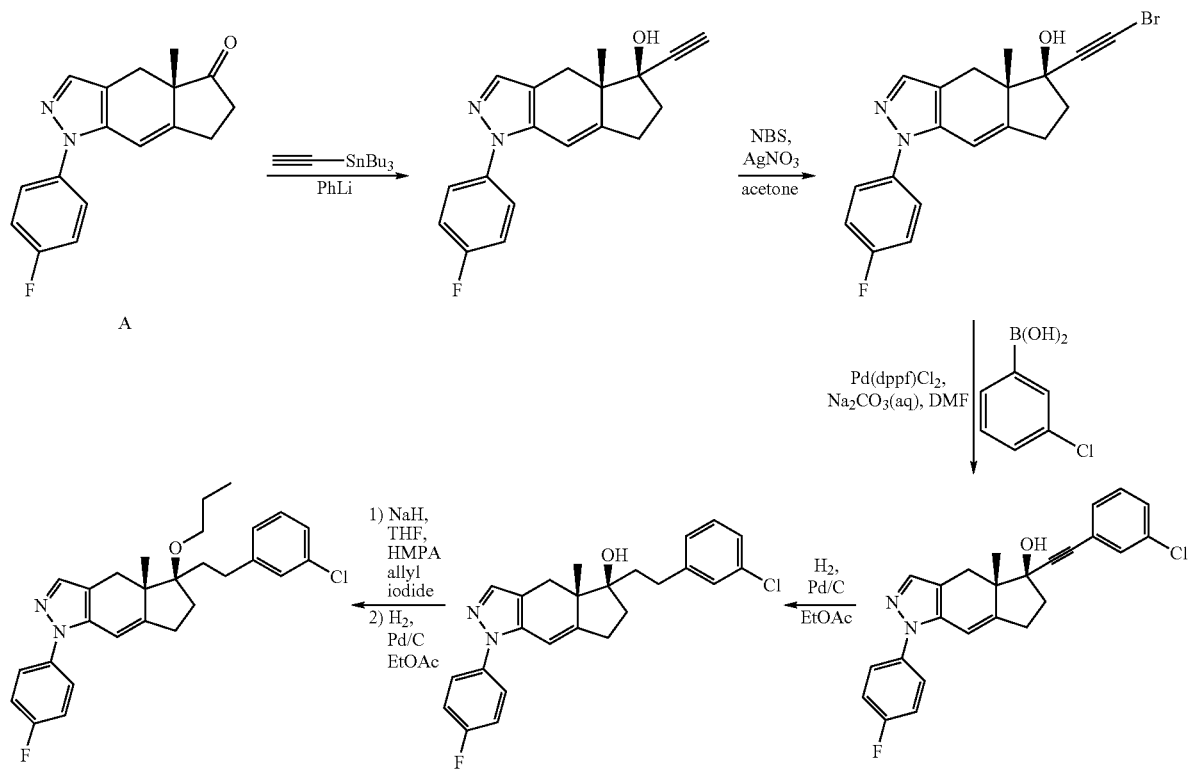
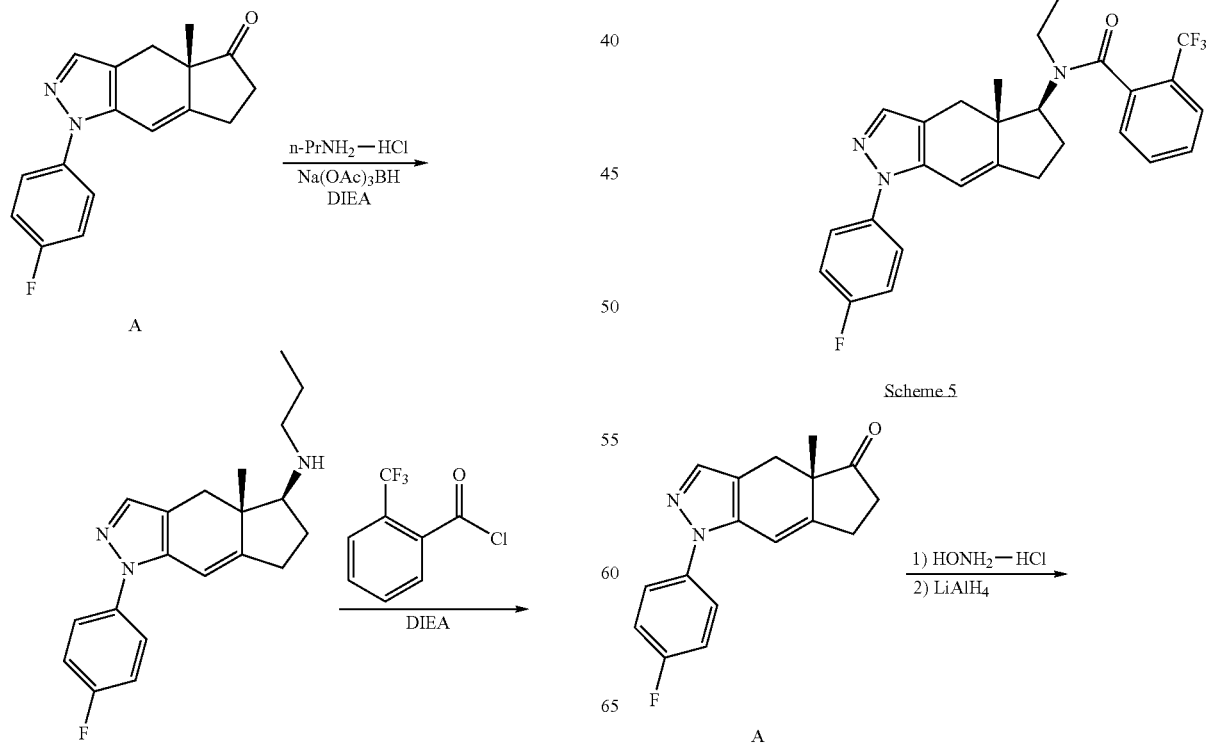

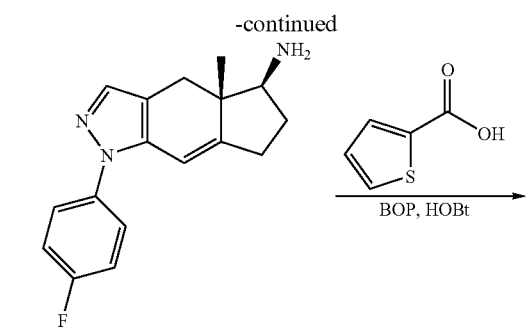
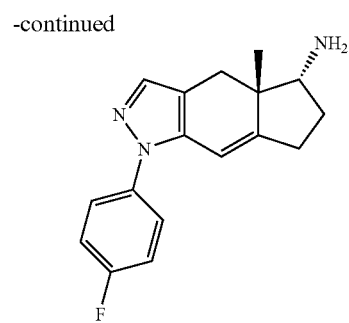
Scheme 7
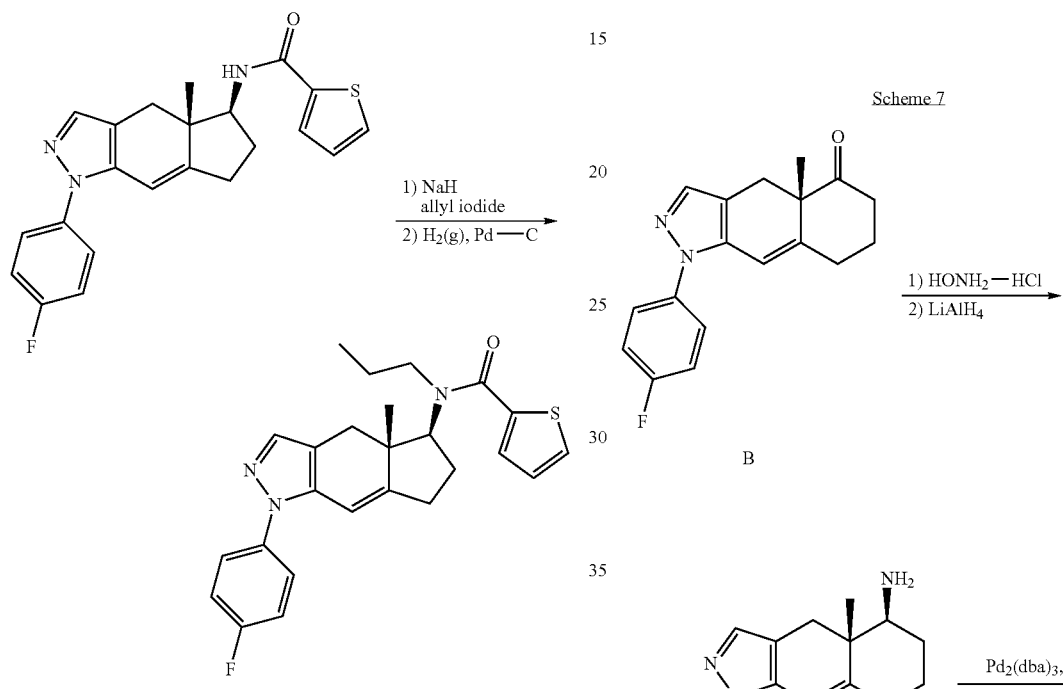
Scheme 6
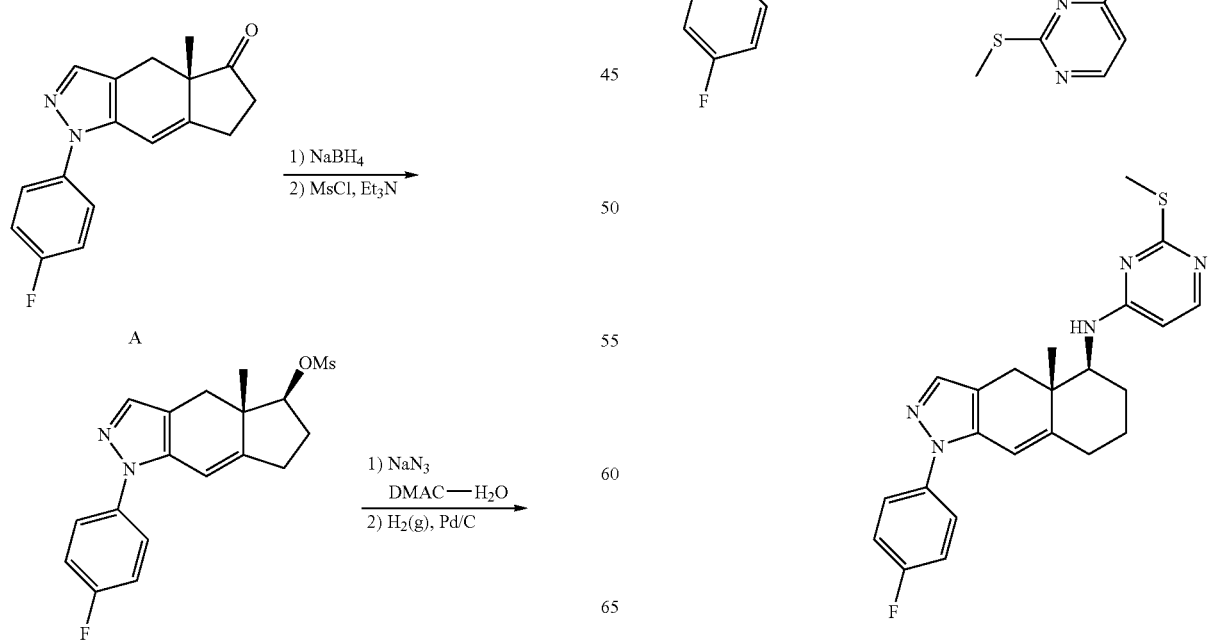

29

Scheme 8

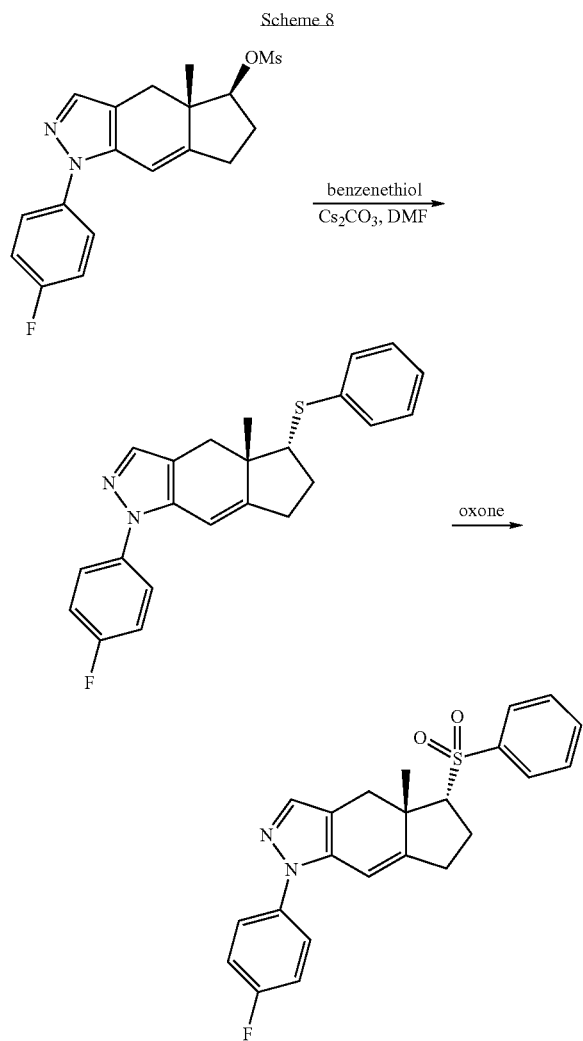

REPRESENTATIVE EXAMPLES

The invention will now be illustrated by the following non-limiting examples in which, unless stated otherwise:

(i) all operations were carried out at room or ambient temperature, that is, at a temperature in the range 18-25° C.;

(ii) evaporation of solvent was carried out using a rotary evaporator under reduced pressure (600-4000 pascals: 4.5-30 mm. Hg) with a bath temperature of up to 60° C.;

(iii) the course of reactions was followed by TLC and/or LCMS and reaction times are given for illustration only;

(iv) the structure and purity of all final products were assured by at least one of the following techniques: TLC, HPLC, MS or NMR spectrometry;

(v) yields, when given, are for illustration only;

(vi) when line-listed, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(vii) chemical symbols have their usual meanings; the following abbreviations have also been used v (volume),

30 w (weight), b.p. (boiling point), m.p. (melting point), L (litre(s)), mL (millilitres), g (gram(s)), mg (milligrams(s)), mol (moles), mmol (millimoles), eq or equiv (equivalent(s)), $IC_{50}$ (molar concentration which results in 50% of maximum possible inhibition), uM (micromolar), nM (nanomolar).

PREPARATIVE EXAMPLES

Compound A

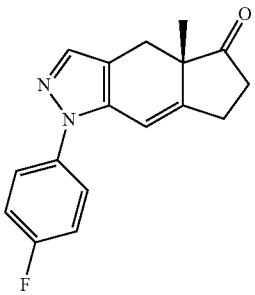

A

COMPOUND A was prepared from the known Hajos-Parrish ketone (*J. Org. Chem.* 1974, 39(12), 1612-1621.) following the same reaction sequence and procedure described below for the preparation of COMPOUND B.

Compound B

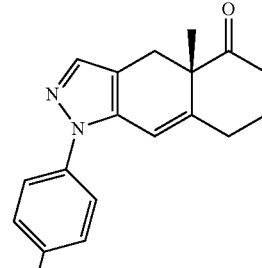

B

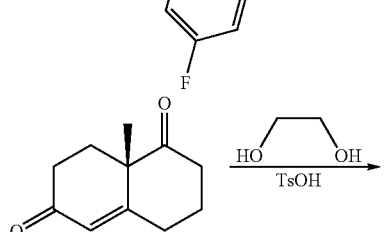

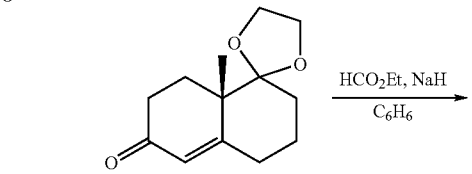

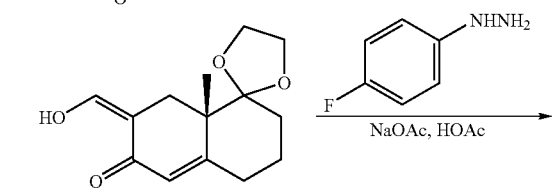

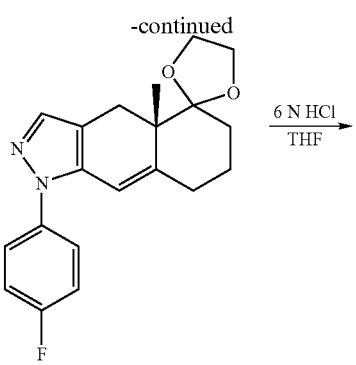

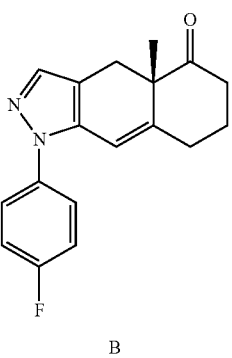

B

Step 1:

4 Å molecular sieves (~5 g) and p-toluenesulfonic acid (5.34 g, 28.05 mmol) were added to a solution of the known Wieland-Miescher ketone (5 g, 28.05 mmol) (*Org. Synth.* 1961, 41, 38; CV-5, 486.) in ethylene glycol (140 mL). After stirring at room temperature for 23 min., the reaction was poured slowly into a 2:1 mixture of ice water/sat. aqueous NaHCO$_3$ (150 mL). The reaction was extracted with EtOAc (4×100 mL) and the combined organic layers were washed with brine (100 mL), dried over MgSO$_4$, filtered and concentrated in vacuo. The residue was purified by flash chromatography (0 to 40% EtOAc/hexanes) on silica gel to afford 5.77 g (93%) of the ketal as a white solid. LCMS=223; (M+1)$^+$. $^1$H NMR (CDCl$_3$, 500 MHz): δ 5.83 (br d, J=1.8 Hz, 1H), 4.43-3.94 (m, 4H), 2.49-2.40 (m, 3H), 2.39-2.27 (m, 2H), 1.95-1.88 (m, 1H), 1.84-1.78 (m, 1H), 1.76-1.64 (m, 3H), 1.37 (s, 3H).

Step 2:

Ethyl formate (7.36 mL, 86.48 mmol) and sodium hydride (60% suspension in mineral oil; 3.46 g, 86.48 mmol) were added to a cooled solution (−40° C.) of the ketal in anhydrous benzene (200 mL). MeOH (450 TL) was added dropwise over 15 min. and the reaction allowed to warm to room temperature. After stirring for 3 h, the reaction was cooled to 0° C. and 50 mL H$_2$O was added. The biphasic system was shaken and the organic layer was washed with H$_2$O (3×50 mL). The combined aqueous layers were washed with diethyl ether (100 mL) and then acidified to pH 5.5-6 with sat. aqueous KH$_2$PO$_4$. The aqueous layer was extracted with EtOAc (5×200 mL). The combined extracts were dried over Na$_2$SO$_4$ and concentrated in vacuo to afford 5.04 g (93%) of hydroxyketone product as an orange oil. LCMS=251; (M+1)$^+$.

Step 3:

The hydroxyketone (4.1 g, 16.4 mmol) was dissolved in glacial acetic acid (40 mL) and parafluorophenylhydrazine hydrochloride (2.8 g, 17.22 mmol) and sodium acetate (1.41 g, 17.22 mmol) were added. After stirring at room temperature for 2 h, the reaction was poured slowly into 10% NaHCO$_3$ (1 L) and extracted with EtOAc (6×500 mL). The combined extracts were washed with brine (500 mL), dried over MgSO$_4$ and concentrated in vacuo. The crude material was purified by flash chromatography (10% EtOAc/hexanes) on silica gel to afford 2.26 g (41%) of the pyrazole ketal as an orange solid. LCMS=421; (M+1)$^+$. $^1$H NMR (CDCl$_3$, 500 MHz): δ 7.47-7.44 (m, 2H), 7.43 (s, 1H), 7.18-7.16 (d, J=8.5 Hz, 1H), 7.16-7.14 (d, J=8.7 Hz, 1H), 6.22 (br d, J=2.2 Hz, 1H), 4.11-4.01 (m, 4H), 3.20-3.16 (d, J=15.7 Hz, 1H), 2.54-2.51 (d, J=16 Hz, 1H), 2.51-2.40 (m, 1H), 2.34-2.28 (m, 1H), 1.88-1.64 (m, 4H), 1.23 (s, 3H).

Step 4:

The pyrazole ketal (2.26 g; 6.65 mmol) was dissolved in THF (65 mL) and 6N HCl (4.43 mL, 26.6 mL) was added. The reaction was heated at 65° C. for 3.5 h and then poured slowly into 10% NaHCO$_3$ (150 mL). The mixture was extracted with EtOAc (4×250 mL) and the combined extracts washed with brine (2×200 mL), dried over MgSO$_4$ and concentrated in vacuo to afford 1.97 g (100%) of COMPOUND B as a brown oil. LCMS=297; (M+1)$^+$. $^1$H NMR (CDCl$_3$, 500 MHz): δ 7.50 (s, 1H), 7.49-7.45 (m, 2H), 7.20-7.16 (m, 2H), 6.31 (br d, J=2 Hz, 1 H), 2.96-2.88 (m, 2H), 2.72-2.62 (m, 2H), 2.59-2.53 (m, 2H), 2.14-2.80 (m, 1H), 1.75-1,64 (qt, J=13.1 Hz, J=4.3 Hz, 1H), 1.27 (s, 3H).

EXAMPLES

Example 1

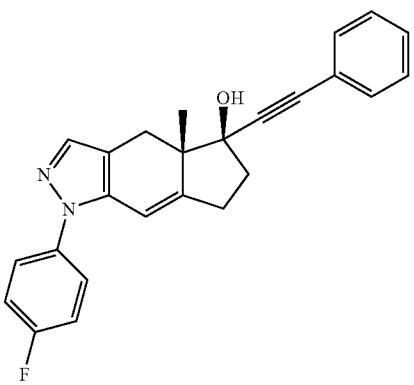

COMPOUND A (1.0 g, 3.53 mmol) was dissolved in 10 mL of anhydrous THF under argon atmosphere and cooled to −50° C. Then 4.0 equiv of phenylethynyl magnesium bromide (1M in THF, 14.12 mmol, 14 mL) was added dropwise. The resulting reaction mixture was then allowed to slowly warm to 23° C. over 6 h. The reaction was quenched with 100 mL of saturated aqueous NH$_4$Cl, extracted with methylene chloride (3×75 mL) and the result organic layers were dried over sodium sulfate and evaporated under reduced pressure. The crude reaction mixture was purified by flash column chromatography (SiO$_2$, EtOAc/hexanes) to give the desired product as a yellow foam. The product was characterized by $^1$H NMR, HPLC and mass spectroscopy (m/z: 385 (M$^+$+1)).

Example 2

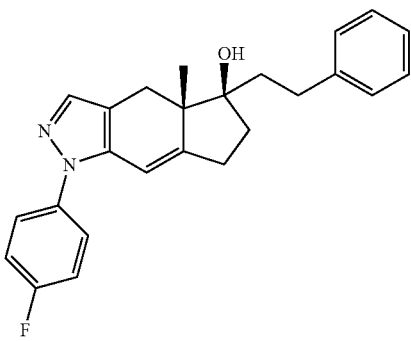

EXAMPLE 1 (408 mg, 1.41 mmol) was dissolved in 10 mL EtOAc and 10% Pd/C (100 mg) was added. The reaction mixture was stirred under hydrogen atmosphere (1 atm) for 20 min before it was filtered through celite, washed with EtOAc (50 mL) and evaporated under reduced pressure. The crude reaction mixture was purified by flash column chromatography (SiO$_2$, acetone/hexanes) to give the desired product as a pale yellow foam. The product was characterized by $^1$H NMR, HPLC and mass spectroscopy (m/z: 389 (M$^+$+1)).

Compound I

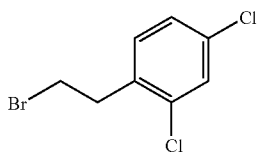

2,4-Dichlorophenethyl alcohol (10 g, 52.0 mmol) was dissolved in 100 mL of methylene chloride, cooled to 0° C. under nitrogen atmosphere and 1.5 equiv of phosphorous tribromide (1M in CH$_2$Cl$_2$, 80 mmol, 80 mL) was added dropwise. The resulting reaction mixture was warmed to 23° C. and stirred for 2 h before the very slow addition of 200 mL of saturated aqueous sodium bicarbonate and extraction with methylene chloride (2×150 mL). The combined organic layers were dried over sodium sulfate and evaporated under reduced pressure. The crude product was purified by a SiO$_2$ plug (5% EtOAc/hexanes) to yield 2,4-dichlorophenethyl bromide. The product was characterized by $^1$H NMR and HPLC.

Compound II

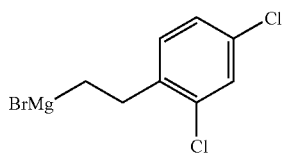

COMPOUND 1 (254 mg, 1.0 mmol) was dissolved in 2 mL THF under an argon atmosphere and 1.0 equiv of magnesium turnings (24 mg, 1 mmol) was added. The resulting suspension was briefly heated then allowed to stir until all the magnesium had reacted (2 h). This 0.5M solution of 2,4-dichlorophenethyl magnesium bromide was used in the following transformation to generate EXAMPLE 3.

Example 3

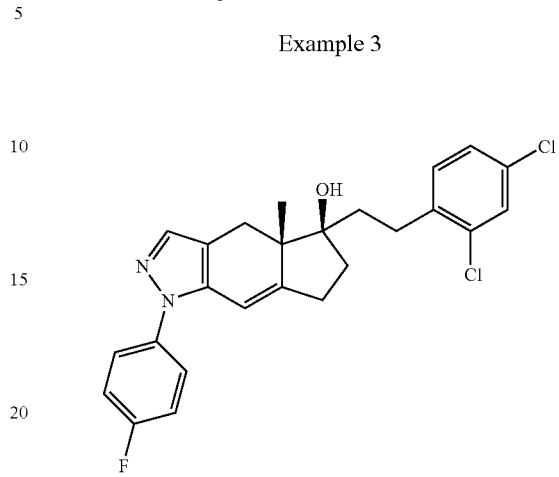

COMPOUND A (100 mg, 0.336 mmol) was dissolved in 2 mL of anhydrous THF under an argon atmosphere and 3.0 equiv anhydrous CeCl$_3$ (1.0 mmol, 246 mg) was added and the resulting suspension was placed in a sonicator at 23° C. for 30 min followed by additional stirring (1 h). This reaction mixture was then cooled to −30° C. and 3.0 equiv of a solution of COMPOUND II (0.5 M in THF, 1.0 mmol, 2 mL) was added. The resulting reaction mixture was allowed to slowly warm to 23° C. over 15 h. The reaction was quenched with 35 mL of IN HCl, extracted with methylene chloride (3×20 mL) and the result organic layers were dried over sodium sulfate and evaporated under reduced pressure. The crude reaction mixture was purified by flash column chromatography (SiO$_2$, EtOAc/hexanes) to give the desired product as a yellow foam. The product was characterized by $^1$H NMR, HPLC and mass spectroscopy (m/z: 457 (M$^+$+1)).

Compound III

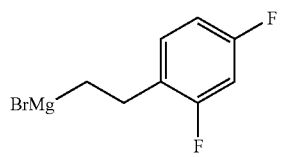

Lithium aluminum hydride (65 g) was suspended in dry THF (1.5 L) under a nitrogen atmosphere and this mixture was then treated with a solution of 2,4-difluorophenylacetic acid (169 g) in dry THF (1 L) over a period of 90 min at 0° C. The reaction mixture was stirred for 70 min at 0° C. and then quenched dropwise with the slow addition of 20% w/v KOH$_{(aq)}$ (340 mL) at 0° C. The inorganic salts were then filtered over Hi flo (200 g) and MgSO$_4$ (200 g), washed with ethyl acetate (200 g), and the filtrate concentrated in vacuo to provide the 2,4-difluorophenethyl alcohol. This alcohol was brominated and converted to its Grignard salt in the same manner described for COMPOUNDS I and II respectively. This 0.5M solution of 2,4difluorophenethyl magnesium bromide was used in the following transformation to generate EXAMPLE 4.

Example 4

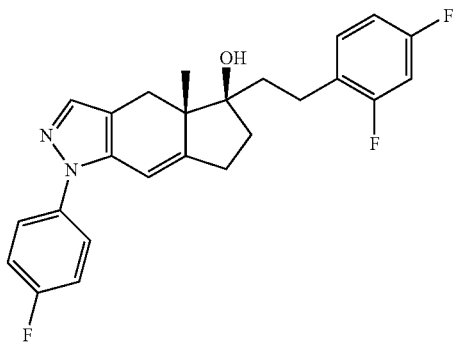

COMPOUND A (200 mg, 0.71 mmol) was dissolved in 4 mL of anhydrous THF under argon atmosphere, cooled to −30° C., and 5.0 equiv of a solution of COMPOUND III (0.5M in THF, 3.54 mmol, 7 mL) was added. The resulting reaction mixture was allowed to slowly warm to 23° C. over 15 h. The reaction was quenched with 50 mL of saturated aqueous $NH_4Cl$, extracted with methylene chloride (3×30 mL) and the result organic layers were dried over sodium sulfate and evaporated under reduced pressure. The crude reaction mixture was purified by flash column chromatography ($SiO_2$, $Et_2O$/hexanes) to give the desired product as a tan foam. The product was characterized by $^1H$ NMR, HPLC and mass spectroscopy (m/z: 425 ($M^+$+1)).

Example 5

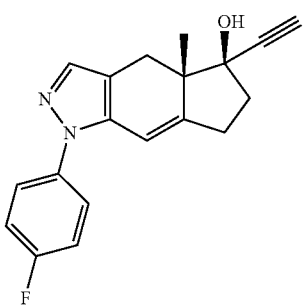

Tributylethynyl tin (6.73 mmol, 16 mL) was dissolved in 40 mL anhydrous THF under an argon atmosphere and cooled to −80° C. Phenyl lithium (1.8M in THF, 56.73 mmol, 32 mL) was added, and the resulting reaction mixture was allowed to stir for 5 min. Then COMPOUND A (4.0 g, 14.18 mmol) in 40 mL anhydrous THF was added dropwise, and the reaction mixture was warmed to 23° C. over 3 h. The reaction was then quenched with 300 mL of saturated aqueous $NH_4Cl$, extracted with methylene chloride (3×100 mL) and the resulting combined organic layers were dried over sodium sulfate and evaporated under reduced pressure. The crude reaction mixture was purified by flash column chromatography ($SiO_2$, EtOAc/hexanes) to give the desired destannylated product as a white foam along with a trace of the tributylstannane product and a minor amount of recovered starting material. The product was characterized by $^1H$ NMR, HPLC and mass spectroscopy (m/z: 309 ($M^+$+1)).

Example 6

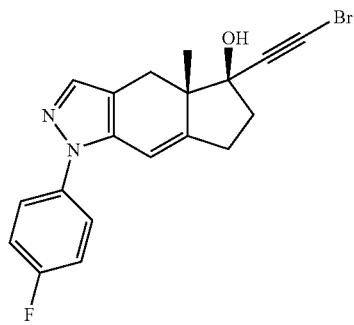

EXAMPLE 5 (4.0 g, 13.05 mmol) was dissolved in acetone and N-bromosuccinimide (15.58 mmol, 2.8 g) and catalytic $AgNO_3$ (50 mg) were added. After 2.5 h, additional N-bromosuccinimide (250 mg) was added. After 1 h the reaction was complete and the reaction mixture was diluted with 300 mL $H_2O$, extracted with EtOAc (3×100 mL) and the resulting combined organic layers were dried over sodium sulfate and evaporated under reduced pressure. The crude reaction mixture was purified by flash column chromatography ($SiO_2$, acetone/hexanes) to give the desired product as a white solid. The product was characterized by $^1H$ NMR, HPLC and mass spectroscopy (m/z: 389 ($M^+$+1)).

Example 7

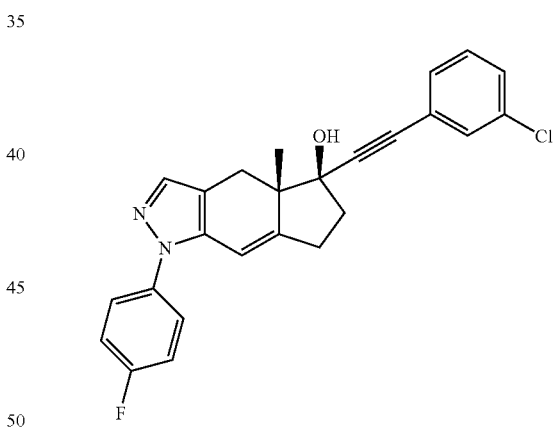

EXAMPLE 6 (4.76 g, 12.33 mmol) was dissolved in 80 mL of degassed DMF under argon atmosphere and 3.0 equiv of aqueous degassed $Na_2CO_3$ (2M, 37.0 mmol, 18 mL), 1.5 equiv of 3-chlorophenyl boronic acid (18.49 mmol, 3.0 g), and dichloro [1,1'-bis(diphenylphosphino)ferrocene]palladium(II) dichloromethane adduct (500 mg) were added. The resulting suspension was heated to 90° C. for 2 h, then quenched by the addition of 400 mL of $H_2O$. The mixture was then extracted with dichloromethane (3×200 mL) and the resulting combined organic layers were dried over sodium sulfate and evaporated under reduced pressure. The crude reaction mixture was purified by flash column chromatography ($SiO_2$, EtOAc/hexanes) to give the desired product as a light orange oil. The product was characterized by $^1H$ NMR, HPLC and mass spectroscopy (m/z: 419 ($M^+$+1)).

Example 8

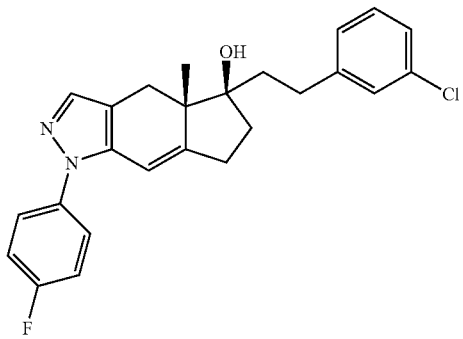

EXAMPLE 7 (3.7 g, 8.88 mmol) was dissolved in 80 mL EtOAc and 10% Pd/C (600mg) was added. The reaction mixture was stirred under hydrogen atmosphere (2 atm) for 6 h before it was filtered through celite, washed with EtOAc (250 mL) and evaporated under reduced pressure. The crude reaction mixture was purified by flash column chromatography ($SiO_2$, acetone/hexanes) to give the desired product as a pale yellow foam. The product was characterized by $^1H$ NMR, HPLC and mass spectroscopy (m/z: 423 ($M^+$+1)).

Example 9

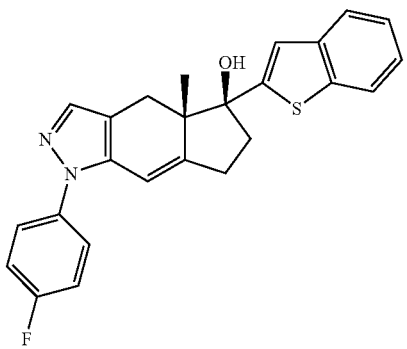

Benzothiophene (3.0 equiv) was dissolved in 2 mL of anhydrous THF under argon atmosphere and cooled to −80° C. Then 3.0 equiv of n-butyl lithium (1.6 M in THF, 0.504 mmol, 0.32 mL) was added. After 15 min, COMPOUND A (50 mg, 0.168 mmol) in 1.0 mL THF was added dropwise and the resulting reaction mixture was then allowed to slowly warm to 23° C. over 6 h. The reaction mixture was quenched with 20 mL of saturated aqueous $NH_4Cl$, extracted with methylene chloride (3×15 mL) and the organic phase was dried over sodium sulfate and evaporated under reduced pressure. The crude reaction mixture was purified by flash column chromatography ($SiO_2$, EtOAc/hexanes) to give the desired product as a yellow foam. The product was characterized by $^1H$ NMR, HPLC and mass spectroscopy (m/z: 417 ($M^+$+1)).

Example 10

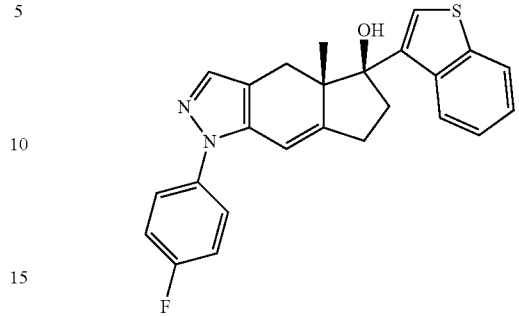

3-Bromobenzothiophene (2.0 equiv) of was dissolved in 2 mL of anhydrous THF under argon atmosphere and cooled to −80° C. and 4.0 equiv of tert-butyl lithium (1.5 M in THF, 0.672 mmol, 0.45 mL) was added. After 5 min, COMPOUND A (50 mg, 0.168 mmol) in 1.0 mL THF was added dropwise and the resulting reaction mixture was slowly warmed to 23° C. over 6 h. The reaction mixture was quenched with 20 mL of saturated aqueous $NH_4Cl$, extracted with methylene chloride (3×15 mL) and the organic phase was dried over sodium sulfate and evaporated under reduced pressure. The crude residue was purified by flash column chromatography ($SiO_2$, EtOAc/hexanes) to give the desired product as a yellow foam. The product was characterized by $^1H$ NMR, HPLC and mass spectroscopy (m/z: 417 ($M^+$+1)).

Example 11

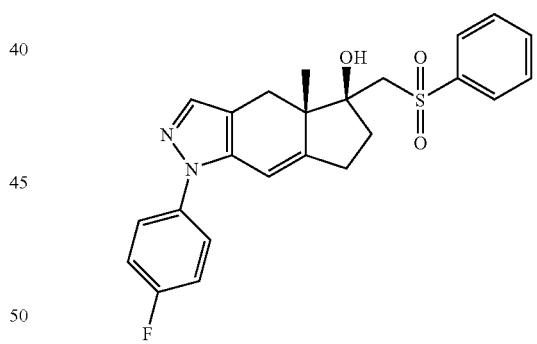

Methyl phenyl sulfone (3 equiv) was dissolved in 1.5 mL of anhydrous THF under an argon atmosphere and cooled to −10° C., and 4.0 equiv of n-butyl lithium (1.5 M in THF, 0.672 mmol, 0.45 mL) was added. After 1 h at 0° C., COMPOUND A (50 mg, 0.168 mmol) in 1.0 mL THF was added dropwise and the resulting reaction mixture was then allowed to slowly warm to 23° C. over 3 h. The reaction mixture was quenched with 20 mL of saturated aqueous $NH_4Cl$, extracted with methylene chloride (3×15 mL) and the organic phase was dried over sodium sulfate and evaporated under reduced pressure. The crude residue was purified by flash column chromatography ($SiO_2$, EtOAc/hexanes) to give the desired product as a yellow foam. The product was characterized by $^1H$ NMR, HPLC and mass spectroscopy (m/z: 439 ($M^+$+1)).

Examples 12-87

The following compounds were prepared under conditions similar to those described in the examples above and illustrated in Schemes 1-3. Where R=H, a sodium borohydride reduction of COMPOUNDS A and B was conducted as described in EXAMPLE 210 below. The following examples were characterized by $^1$H NMR, HPLC and mass spectrometry.

| EX. | n | R Group | MS (m/z) (M$^+$ + 1) |
|---|---|---|---|
| 12 | 1 | vinyl | 311 |
| 13 | 2 | vinyl | 325 |
| 14 | 1 | allyl | 325 |
| 15 | 2 | allyl | 339 |
| 16 | 1 | 3-butenyl | 339 |
| 17 | 2 | 3-butenyl | 353 |
| 18 | 2 | n-butyl | 355 |
| 19 | 1 | n-pentyl | 355 |
| 20 | 2 | n-pentyl | 369 |
| 21 | 2 | n-hexyl | 383 |
| 22 | 1 | 3-methylbutyl | 355 |
| 23 | 2 | 3-methylbutyl | 369 |
| 24 | 1 | 2-cyclohexylethyl | 395 |
| 25 | 2 | 2-cyclohexylethyl | 409 |
| 26 | 1 | 3,3-dimethylbutyl | 369 |
| 27 | 2 | 3,3-dimethylbutyl | 383 |
| 28 | 1 | 4-methyl-3-pentenyl | 367 |
| 29 | 2 | 4-methyl-3-pentenyl | 381 |
| 30 | 1 | 4,4,4-trifluorobutyl | 395 |
| 31 | 2 | 4,4,4-trifluorobutyl | 409 |
| 32 | 1 | 3,4,4-trifluoro-3-butenyl | 393 |
| 33 | 2 | 3,4,4-trifluoro-3-butenyl | 407 |
| 34 | 1 | 3-methoxypropyl | 357 |
| 35 | 2 | 3-methoxypropyl | 371 |
| 36 | 2 | benzyl | 389 |
| 37 | 2 | phenyl | 375 |
| 38 | 2 | phenethyl | 403 |
| 39 | 2 | 3-phenylpropyl | 417 |
| 40 | 1 | 2-(2-chlorophenyl)ethyl | 423 |
| 41 | 2 | 2-(2-chlorophenyl)ethyl | 437 |
| 42 | 2 | 2-(3-chlorophenyl)ethyl | 437 |
| 43 | 1 | 2-(4-chlorophenyl)ethyl | 423 |
| 44 | 2 | 2-(4-chlorophenyl)ethyl | 437 |
| 45 | 2 | 2-(2,4-dichlorophenyl)ethyl | 471 |
| 46 | 1 | 2-(4-fluorophenyl)ethyl | 407 |
| 47 | 2 | 2-(4-fluorophenyl)ethyl | 421 |
| 48 | 1 | 2-(2,5-difluorophenyl)ethyl | 425 |
| 49 | 1 | 2-(2,3-difluorophenyl)ethyl | 425 |
| 50 | 1 | 2-(3,5-difluorophenyl)ethyl | 425 |
| 51 | 1 | 2-(4-methoxyphenyl)ethyl | 419 |
| 52 | 2 | 2-(4-methoxyphenyl)ethyl | 433 |
| 53 | 1 | 2-(2-naphthyl)ethyl | 439 |
| 54 | 2 | 2-(2-naphthyl)ethyl | 453 |
| 55 | 2 | 2-(2,4-difluorophenyl)ethyl | 439 |
| 56 | 1 | 2-(3-(trifluoromethyl)phenyl)ethyl | 457 |
| 57 | 2 | 2-(3-(trifluoromethyl)phenyl)ethyl | 471 |
| 58 | 1 | 2-(2-methoxyphenyl)ethyl | 419 |
| 59 | 2 | 2-(2-methoxyphenyl)ethyl | 433 |
| 60 | 1 | 2-(4-tert-butylphenyl)ethyl | 445 |

-continued

| EX. | n | R Group | MS (m/z) (M$^+$ + 1) |
|---|---|---|---|
| 61 | 2 | 2-(4-tert-butylphenyl)ethyl | 459 |
| 62 | 1 | 2-(4-methylphenyl)ethyl | 403 |
| 63 | 2 | 2-(4-methylphenyl)ethyl | 417 |
| 64 | 1 | 2-(1-naphthyl)ethyl | 439 |
| 65 | 2 | 2-(1-naphthyl)ethyl | 453 |
| 66 | 1 | 2-(2-methylphenyl)ethyl | 403 |
| 67 | 2 | 2-(2-methylphenyl)ethyl | 417 |
| 68 | 1 | 2-(3-methylphenyl)ethyl | 403 |
| 69 | 2 | 2-(3-methylphenyl)ethyl | 417 |
| 70 | 1 | 2-(2-fluorophenyl)ethyl | 407 |
| 71 | 1 | 2-(3-fluorophenyl)ethyl | 407 |
| 72 | 1 | 2-(3,4-dichlorophenyl)ethyl | 458 |
| 73 | 1 | 2-(2-chloro-4-fluorophenyl)ethyl | 441 |
| 74 | 1 | 2-(3-thiopheneyl)ethyl | 395 |
| 75 | 1 | 3-(N-pyrrolyl)propyl | 392 |
| 76 | 2 | 3-(N-pyrrolyl)propyl | 406 |
| 77 | 1 | E-2-phenylethenyl | 387 |
| 78 | 2 | E-2-phenylethenyl | 401 |
| 79 | 1 | Z-2-phenylethenyl | 387 |
| 80 | 2 | Z-2-phenylethenyl | 401 |
| 81 | 2 | 2-phenylethynyl | 399 |
| 82 | 1 | 2-(2,4-difluorophenyl)ethynyl | 421 |
| 83 | 1 | 2-(2-thiopheneyl)ethyl | 395 |
| 84 | 1 | 2-(3,4-difluorophenyl)ethyl | 425 |
| 85 | 1 | 2-(3,4,5-trifluorophenyl)ethyl | 443 |
| 86 | 2 | H | 299 |
| 87 | 1 | H | 285 |

Example 88

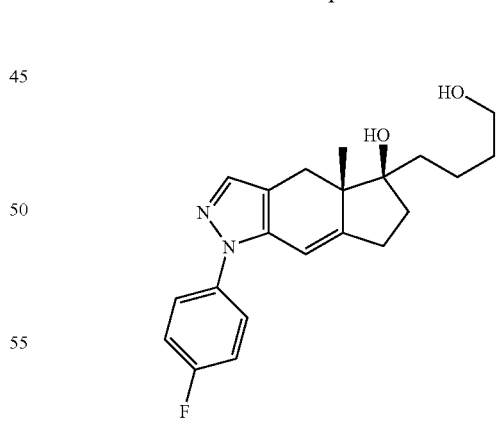

EXAMPLE 17 (14 mg, 0.039 mmol) was dissolved in 1.0 mL THF under argon atmosphere and cooled to 0° C. and 4.0 equiv of 9-BBN (0.5M in THF, 0.156 mmol, 0.312 mL) were added. The reaction mixture was allowed to warm to 23° C. and stir for 15 h before being quenched by the addition of 1 mL of ethanol, 0.052 mL of 6N aqueous NaOH, and 0.1 mL of 30% aqueous hydrogen peroxide. The reaction was then diluted with 5.0 mL of water, extracted with methylene chlo- Example 89

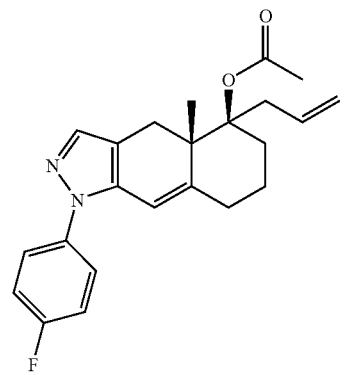

EXAMPLE 15 (60 mg, 0.178 mmol) was dissolved in 2.0 mL THF under argon atmosphere and cooled to −10° C. and 2.0 equiv of methyl magnesium bromide (1.0M in THF, 0.356 mmol, 0.35 mL) was added. After 5 min, acetic anhydride (0.267 mmol, 0.25 mL) was added and the resulting reaction mixture was warmed to 65° C. for 15 h. The reaction was then quenched with 10 mL of saturated aqueous $NH_4Cl$, extracted with methylene chloride (3×10 mL) and the organic phase was dried over sodium sulfate and evaporated under reduced pressure. The crude reaction mixture was purified by flash column chromatography ($SiO_2$, EtOAc/hexanes) to give the desired product as a white foam. The product was characterized by $^1H$ NMR, HPLC and mass spectroscopy (m/z: 381 ($M^+$+1)).

Example 90

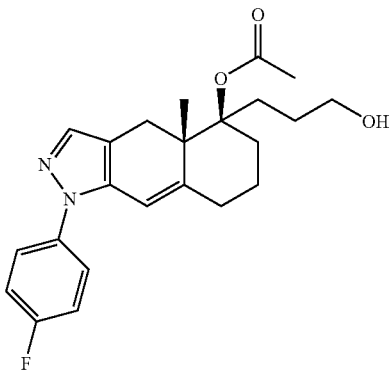

EXAMPLE 90 was prepared from EXAMPLE 89 according to the above procedure described in EXAMPLE 88. The product was characterized by $^1H$ NMR, HPLC and mass spectroscopy (m/z: 399 ($M^+$+1)).

Example 91

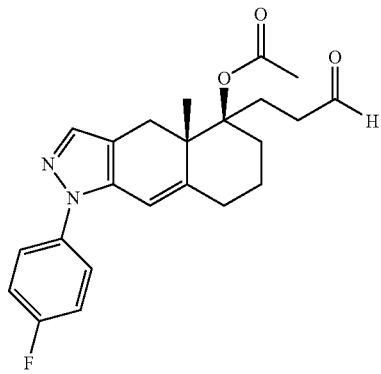

EXAMPLE 90 (25 mg, 0.059 mmol) was dissolved in 2.0 mL methylene chloride under an argon atmosphere and cooled to 0° C. Then 20 equiv of pyridine (1.18 mmol, 0.094 mL) and 3.0 equiv of Dess-Martin periodinane (0.177 mmol, 75 mg) were added, and the resulting reaction mixture was slowly warmed to 23° C. over 3 h. The reaction was quenched with 20 mL of saturated aqueous $NH_4Cl$, extracted with methylene chloride (3×15 mL) and the organic phase was dried over sodium sulfate and evaporated under reduced pressure. The crude residue was purified by flash column chromatography ($SiO_2$, EtOAc/hexanes) to give the desired product as a yellow oil. The product was characterized by $^1H$ NMR, HPLC and mass spectroscopy (m/z: 397 ($M^+$+1)).

Example 92

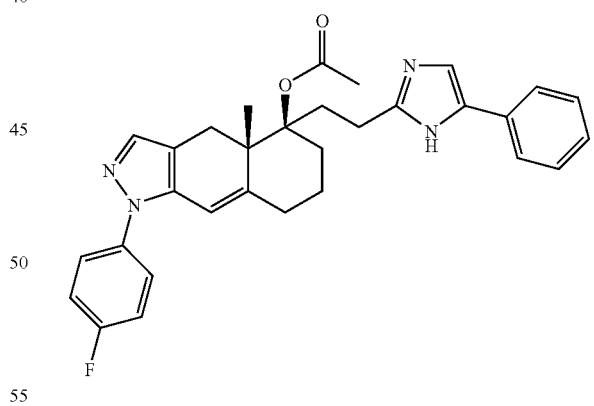

EXAMPLE 91 (15 mg, 0.038 mmol) was dissolved in 1.0 mL MeOH under an argon atmosphere, and 10 equiv of ammonium acetate (0.38 mmol, 30 mg) and 3.0 equiv of phenyl glyoxal (0.114 mmol, 16 mg) were added. The resulting reaction mixture was heated at 65° C. for 15 h, cooled and evaporated under reduced pressure. The crude residue was then purified by flash column chromatography ($SiO_2$, ethyl ether/hexanes) to give the desired product as a yellow foam. The product was characterized by $^1H$ NMR, HPLC and mass spectroscopy (m/z: 511 ($M^+$+1)).

Example 93

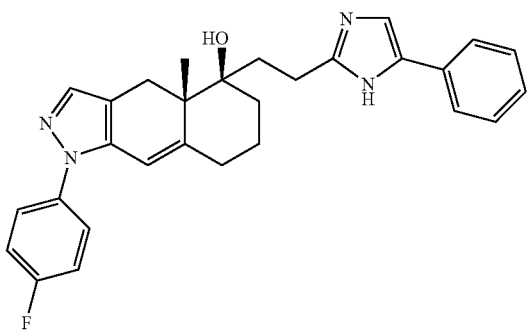

EXAMPLE 92 (7 mg, 0.014 mmol) was dissolved in 0.5 mL anhydrous MeOH and cooled to 0° C. and 2.0 equiv of potassium carbonate (0.027 mmol, 4.0 mg) was added. After 2 h the reaction mixture was diluted with 10 mL of water, extracted with methylene chloride (3×10 mL) and the organic phase was dried over sodium sulfate and evaporated under reduced pressure. The crude residue was purified by flash column chromatography ($SiO_2$, EtOAc/hexanes) to give the desired product as a yellow film. The product was characterized by $^1H$ NMR, HPLC and mass spectroscopy (m/z: 469 ($M^+$+1)).

Example 94

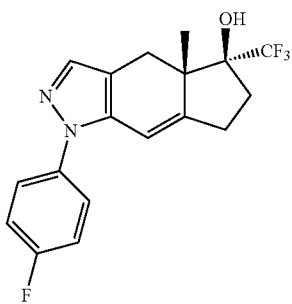

COMPOUND A (50 mg, 0.168 mmol) was dissolved in 1.0 mL THF under an argon atmosphere and $(CF_3)Si(CH_3)_3$ [0.5 M in THF] (0.504 mmol, 1.0 mL) followed by catalytic tetrabutylammonium fluoroide [1 M in THF] (0.005 mL) were added. The resulting reaction mixture was allowed to stir for 15 hours before being diluted with 25 mL of aqueous 1N HCl, extracted with methylene chloride (3×20 mL), and the organic phase was dried over anhydrous sodium sulfate and evaporated under reduced pressure. The crude residue was purified by flash column chromatography ($SiO_2$, EtOAc/hexanes) to give the desired product as a yellow oil. The product was characterized by $^1H$ NMR, HPLC and mass spectroscopy (m/z: 353 ($M^+$+1)).

Example 95

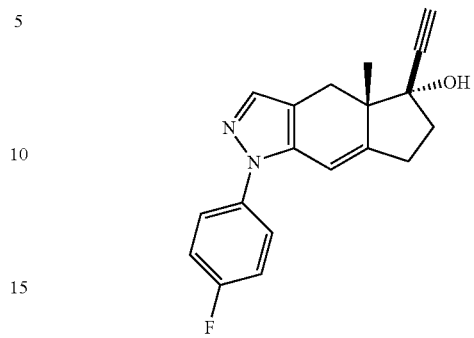

EXAMPLE 5 was acetylated under conditions described for EXAMPLE 89. This propargylic acetate (20 mg, 0.168 mmol) was dissolved in 0.5 mL THF under an argon atmosphere and benzylamine (0.11 mmol, 0.12 mL) followed by catalytic copper (1) chloride (3 mg) were added. The resulting reaction mixture was heated at 100° C. in a sealed tube for 2 hours before it was cooled to room temperature, diluted with 20 mL of $H_2O$, extracted with methylene chloride (3×20 mL), and the organic phase was dried over anhydrous sodium sulfate and evaporated under reduced pressure. The crude residue was purified by flash column chromatography ($SiO_2$, EtOAc/hexanes) to give the desired product as a clear oil. The product was characterized by $^1H$ NMR, HPLC and mass spectroscopy (m/z: 309 ($M^+$+1)).

Example 96

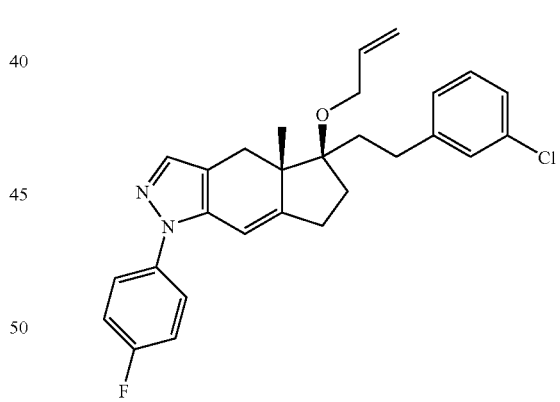

EXAMPLE 8 (3.0 g, 7.10 mmol) was dissolved in 40 mL of 5:1 THF/HMPA under argon atmosphere and sodium hydride (60% in mineral oil, 28.44 mmol, 1.0 g) was added and the reaction mixture was allowed to stir for 10 min at 23° C. Allyl iodide (35.54 mmol, 3.2 mL) was then added and the reaction was heated to 100° C. for 3 h before cooling to 23° C. The reaction was then quenched by the addition of 250 mL of saturated aqueous $NH_4Cl$, extracted with methylene chloride (3×100 mL) and the result organic layers were dried over sodium sulfate and evaporated under reduced pressure. The crude reaction mixture was purified by flash column chromatography (SiO$_2$, acetone/hexanes) to give the desired product as an orange foam. The product was characterized by $^1$H NMR, HPLC and mass spectroscopy (m/z: 463 (M$^+$+1)).

Example 97

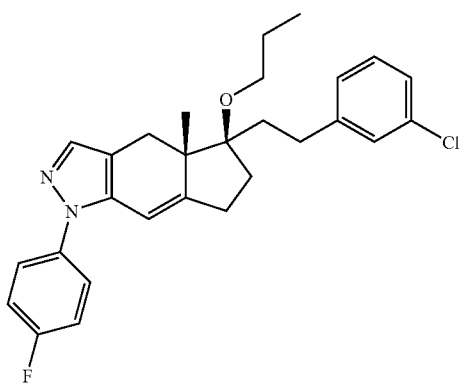

EXAMPLE 96 (2.32 g, 5.02 mmol) was dissolved in 30 mL EtOAc and 10% Pd/C (300 mg) was added. The reaction mixture was stirred under a hydrogen atmosphere (1 atm) for 2 h before it was filtered through celite, washed with EtOAc (200 mL) and evaporated under reduced pressure. The crude reaction mixture was purified by flash column chromatography (SiO$_2$, acetone/hexanes) to give the desired product as a white foam. The product was characterized by $^1$H NMR, HPLC and mass spectroscopy (m/z: 465 (M$^+$+1)).

Examples 98-125

The following compounds were prepared under conditions similar to those described in the examples above and illustrated in Scheme 3. Other alkyl halides known to those skilled in the art were used in place of allyl iodide to generate the ethers shown in the table below. As described in EXAMPLE 97, hydrogenation was also used to generate some of the saturated ethers shown in the table below. The following examples were characterized by $^1$H NMR, HPLC and mass spectrometry.

| EX. | n | R$^i$ Group | R$^{ii}$ Group | MS (m/z) (M$^+$ + 1) |
|---|---|---|---|---|
| 98 | 1 | H | n-propyl | 327 |
| 99 | 2 | allyl | allyl | 379 |
| 100 | 1 | phenethyl | cyclopropylmethyl | 443 |
| 101 | 1 | phenethyl | E-2-butenyl | 443 |

-continued

| EX. | n | R$^i$ Group | R$^{ii}$ Group | MS (m/z) (M$^+$ + 1) |
|---|---|---|---|---|
| 102 | 1 | 2-(2,4-dichlorophenyl)ethyl | methyl | 471 |
| 103 | 1 | 2-(2-chlorophenyl)ethyl | methyl | 437 |
| 104 | 1 | 2-(3-chlorophenyl)ethyl | methyl | 437 |
| 105 | 1 | n-pentyl | methyl | 369 |
| 106 | 1 | 2-(4-fluorophenyl)ethyl | methyl | 421 |
| 107 | 2 | phenethyl | methyl | 417 |
| 108 | 1 | 2-(2,4-dichlorophenyl)ethyl | benzyl | 547 |
| 109 | 1 | 2-(2,4-dichlorophenyl)ethyl | allyl | 497 |
| 110 | 1 | 2-(2,4-dichlorophenyl)ethyl | n-propyl | 499 |
| 111 | 1 | 2-(2-chlorophenyl)ethyl | n-propyl | 465 |
| 112 | 1 | phenethyl | n-propyl | 431 |
| 113 | 1 | phenethyl | methyl | 403 |
| 114 | 1 | 2-(3-chlorophenyl)ethynyl | allyl | 459 |
| 115 | 1 | 2-(3-chlorophenyl)ethynyl | n-propyl | 461 |
| 116 | 1 | 2-(2,4-difluorophenyl)ethyl | methyl | 439 |
| 117 | 2 | 2-(2,4-difluorophenyl)ethyl | methyl | 453 |
| 118 | 1 | phenethyl | E-2-pentenyl | 457 |
| 119 | 1 | trifluoromethyl | allyl | 393 |
| 120 | 1 | trifluoromethyl | n-propyl | 395 |
| 121 | 1 | 2-(3-methylphenyl)ethyl | methyl | 417 |
| 122 | 1 | phenethyl | n-butyl | 445 |
| 123 | 1 | phenethyl | n-pentyl | 459 |
| 124 | 1 | 2-(3,4-difluorophenyl)ethyl | n-propyl | 467 |
| 125 | 1 | 2-(3-fluorophenyl)ethyl | methyl | 421 |

Example 126

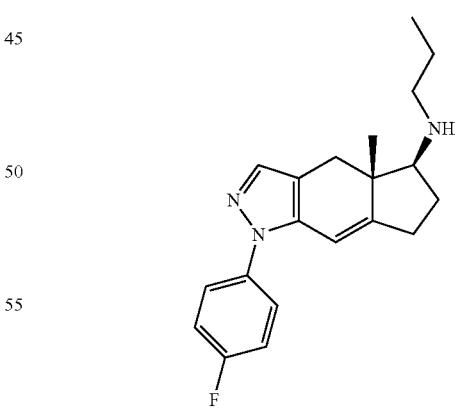

COMPOUND A (250 mg, 0.88 mmol) was diluted into CH$_2$Cl$_2$ (11 mL), and treated with n-propylamine hydrochloride (842 mg, 8.87 mmol), diisopropylethylamine (2.4 mL, 13.3 mmol), and followed by sodium triacetoxyborohydride (376 mg, 1.77 mmol). The reaction mixture was maintained at 23° C. for 15 h. The mixture was then partitioned between NaHCO$_{3(aq)}$ and CH$_2$Cl$_2$, and the organic phase was dried over anhydrous sodium sulfate and concentrated in vacuo. The crude product was either used directly in subsequent reactions or purified by flash chromatography (BIOTAGE® 40S, SiO$_2$, 1:9:90 NH$_4$OH-MeOH—CHCl$_3$) to provide the product which was characterized by $^1$H NMR, HPLC and mass spectrometry (m/z: 326 (M$^+$+1)).

Example 127

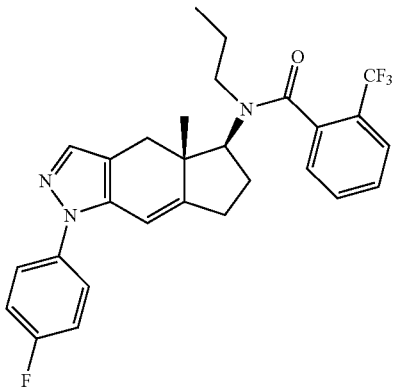

EXAMPLE 126 (2 g, 6.15 mmol) was diluted into CH$_2$Cl$_2$ (31 mL) and treated with diisopropylethylamine (2.3 mL, 12.3 mmol), followed by 2-(trifluoromethyl)benzoyl chloride (1.4 mL, 9.23 mmol). The reaction mixture was maintained at 23° C. for 2 h. The mixture was then partitioned between NaHCO$_{3(aq)}$ and CH$_2$Cl$_2$, the organic phase dried over anhydrous sodium sulfate, concentrated in vacuo and purified by flash chromatography (BIOTAGE® 65M, SiO$_2$, 30% EtOAc-hexane) to provide the product which was characterized by $^1$H NMR, HPLC and mass spectrometry (m/z: 498 (M$^+$+1)).

Example 128

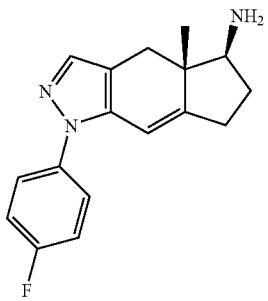

COMPOUND A (200 mg, 0.71 mmol) was diluted into pyridine (2 mL), treated with hydroxylamine hydrochloride (56 mg, 0.81 mmol), and the mixture heated at 90° C. for 2 h. The reaction mixture was then partitioned between 0.01N HCl$_{(aq)}$ and CH$_2$Cl$_2$, the organic phase dried over anhydrous sodium sulfate and concentrated in vacuo. The crude oxime intermediate was diluted into anhydrous THF (6 mL) and treated with solid lithium aluminum hydride (230 mg, 6.05 mmol). The reaction mixture was maintained at 23° C. for 16 h, partitioned between (1:1) Rochelle's salt/NaHCO$_{3(aq)}$ and CHCl$_3$, the organic phase dried over anhydrous sodium sulfate and concentrated in vacuo. The crude primary amine which was characterized by $^1$H NMR, HPLC and mass spectrometry (m/z: 284 (M$^+$+1)) was used directly in subsequent reactions.

Example 129

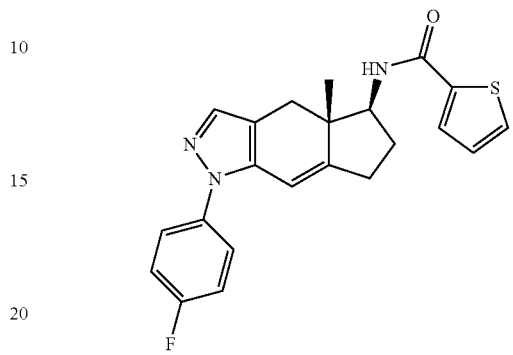

EXAMPLE 128 (6 mg, 0.021 mmol) was diluted into CH$_2$Cl$_2$ (0.5 mL), treated with 2-thiophenecarboxylic acid (8 mg, 0.064 mmol), diisopropylethylamine (0.018 mL, 0.11 mmol), 1-hydroxybenzotriazole (14 mg, 0.11 mmol) and lastly BOP reagent (34 mg, 0.076 mmol). The mixture was maintained at 25° C. for 4 h, then partitioned between NaHCO$_{3(aq)}$ and CH$_2$Cl$_2$, the organic phase dried over anhydrous sodium sulfate, concentrated in vacuo and purified by preparative thin layer chromatography (500 micron SiO$_2$, 20×20 cm, 30% EtOAc-hexane) to provide the product which was characterized by $^1$H NMR, HPLC and mass spectrometry (m/z: 394 (M$^+$+1)).

Example 130

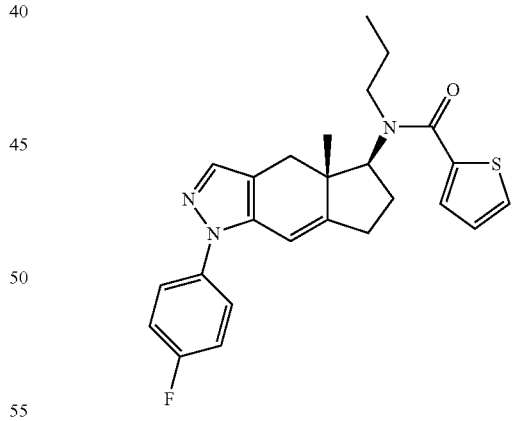

Sodium hydride (13 mg, 0.530 mmol) was tared, diluted with a THF (0.5 mL) solution of EXAMPLE 129 (21 mg, 0.053 mmol) and then treated with allyl iodide (0.025 mL, 0.265 mmol). The mixture was maintained at 25° C. for 12 h, then partitioned between NH$_4$Cl$_{(aq)}$ and CHCl$_3$, the organic phase dried over anhydrous sodium sulfate, and concentrated in vacuo. The crude N-allyl amide was diluted into ethyl acetate (1 mL) and treated with catalytic 10% Pd—C. The system was fitted with a balloon of hydrogen gas, and the mixture stirred under an atmosphere of H$_2$ at 25° C. for 1 h. The mixture was then filtered over celite, washed with EtOAc, and the filtrate concentrated in vacuo. The residue was purified by preparative thin layer chromatography (500 micron SiO$_2$, 20×20 cm, 30% EtOAc-hexane) to provide the product which was characterized by $^1$H NMR, HPLC and mass spectrometry (m/z: 436 (M$^+$+1)).

Examples 131-209

The following compounds were prepared under conditions similar to those described in the examples above and illustrated in Schemes 4 and 5. Methyl iodide or methylamine hydrochloride was used in place of allyl iodide or n-propylamine hydrochloride respectively to generate the N-methyl analogs shown in the table below. For examples other than amides, a chloroformate or isocyanate or sulfonyl chloride was used to generate carbamates or ureas or sulfonamides respectively shown in the table below. The following examples were characterized by $^1$H NMR, HPLC and mass spectrometry.

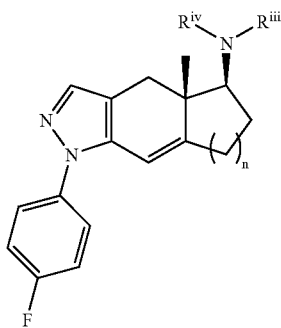

| EX. | n | R$^{iii}$ Group | R$^{iv}$ Group | MS (m/z) (M$^+$ + 1) |
|---|---|---|---|---|
| 131 | 1 | CO(3,3,3-trifluoropropyl) | H | 408 |
| 132 | 1 | CO(2-(trifluoromethyl)phenyl) | H | 456 |
| 133 | 1 | CO(3-chlorophenyl) | H | 422 |
| 134 | 1 | COCH$_2$(2-(trifluoromethyl)phenyl) | H | 470 |
| 135 | 1 | CO(2,4,5-trifluorophenyl) | H | 442 |
| 136 | 1 | CO(3-thipheneyl) | H | 394 |
| 137 | 1 | COCH$_2$(2,4-difluorophenyl) | H | 438 |
| 138 | 1 | COCH$_2$(3-chlorophenyl) | H | 436 |
| 139 | 1 | CO(3-chloro-4-fluorophenyl) | H | 440 |
| 140 | 1 | COCH$_2$(2,5-difluorophenyl) | H | 438 |
| 141 | 1 | COCH$_2$(2-thipheneyl) | H | 408 |
| 142 | 1 | COCH$_2$(3-thipheneyl) | H | 408 |
| 143 | 1 | CO(2-chloro-5-fluorophenyl) | H | 440 |
| 144 | 1 | COCH$_2$(3-chloro-4-fluorophenyl) | H | 454 |
| 145 | 1 | CO(2,4,5-trifluorophenyl) | methyl | 456 |
| 146 | 1 | CO(2-(trifluoromethyl)phenyl) | methyl | 470 |
| 147 | 1 | CO(2-thipheneyl) | methyl | 408 |
| 148 | 1 | CO(3-chlorophenyl) | methyl | 436 |
| 149 | 1 | CO(phenyl) | H | 388 |
| 150 | 1 | CO(2,4-difluorophenyl) | H | 424 |
| 151 | 1 | COCH$_2$(3-chloro-4-fluorophenyl) | methyl | 468 |
| 152 | 1 | CO(2,4-difluorophenyl) | methyl | 438 |
| 153 | 1 | COCH$_2$(2-(trifluoromethyl)phenyl) | methyl | 484 |
| 154 | 1 | CO(2-fluorophenyl) | H | 406 |
| 155 | 1 | CO(2,6-difluorophenyl) | H | 424 |
| 156 | 1 | CO(2-chlorophenyl) | H | 422 |
| 157 | 1 | CO(1-naphthyl) | H | 438 |
| 158 | 1 | CO(2-(trifluoromethyl)-4-fluorophenyl) | H | 474 |
| 159 | 1 | CO(2,5-difluorophenyl) | H | 424 |
| 160 | 1 | CO(2,3-difluorophenyl) | H | 424 |
| 161 | 1 | CO(2-chloro-4-fluorophenyl) | H | 440 |
| 162 | 1 | CO(2-chloro-3-fluorophenyl) | H | 440 |
| 163 | 1 | CO(tert-butyl) | H | 368 |
| 164 | 1 | CO(isopropyl) | H | 354 |
| 165 | 1 | CO(2-chloro-3-fluorophenyl) | methyl | 454 |
| 166 | 1 | CO(2-(trifluoromethyl)-4-fluorophenyl) | methyl | 488 |
| 167 | 1 | CO(2,6-difluorophenyl) | methyl | 438 |
| 168 | 1 | CO(2-chloro-4-fluorophenyl) | methyl | 454 |
| 169 | 1 | SO$_2$(phenyl) | H | 424 |
| 170 | 1 | CO(2,6-dichlorophenyl) | methyl | 470 |
| 171 | 1 | CO(2,6-dichlorophenyl) | H | 456 |
| 172 | 2 | CO(phenyl) | H | 402 |
| 173 | 2 | CO(2-(trifluoromethyl)phenyl) | H | 470 |
| 174 | 2 | CO(2-chloro-4-fluorophenyl) | H | 454 |
| 175 | 2 | CO(2-chlorophenyl) | H | 436 |
| 176 | 2 | CO(2-fluorophenyl) | H | 420 |
| 177 | 2 | COCH$_2$(2-(trifluoromethyl)phenyl) | H | 484 |
| 178 | 2 | COCH$_2$(2,4-difluorophenyl) | H | 452 |
| 179 | 2 | COCH$_2$(3-chlorophenyl) | H | 450 |
| 180 | 1 | SO$_2$(2,4-difluorophenyl) | H | 460 |
| 181 | 1 | CO(2,4-difluorophenyl) | n-propyl | 466 |
| 182 | 1 | SO$_2$(3-chlorophenyl) | H | 458 |
| 183 | 2 | CO(3-chlorophenyl) | H | 436 |
| 184 | 1 | SO$_2$(2-chloro-4-fluorophenyl) | H | 476 |
| 185 | 1 | CO$_2$(phenyl) | methyl | 418 |
| 186 | 1 | CO$_2$(phenyl) | H | 404 |
| 187 | 1 | CONH(phenyl) | H | 403 |
| 188 | 1 | SO$_2$(2-fluorophenyl) | H | 442 |
| 189 | 1 | SO$_2$(2-chlorophenyl) | H | 458 |
| 190 | 1 | CONH(phenyl) | methyl | 417 |
| 191 | 1 | SO$_2$(2-(trifluoromethyl)phenyl) | H | 492 |
| 192 | 2 | CONH(phenyl) | H | 417 |
| 193 | 1 | SO$_2$(3-fluorophenyl) | H | 442 |
| 194 | 2 | CO$_2$(phenyl) | H | 418 |
| 195 | 2 | CO(2,4-difluorophenyl) | H | 438 |
| 196 | 1 | CO(2-chloro-4-fluorophenyl) | n-propyl | 482 |
| 197 | 2 | CO(2-(trifluoromethyl)-4-fluorophenyl) | H | 488 |
| 198 | 2 | CO(2-chloro-4-fluorophenyl) | methyl | 468 |
| 199 | 2 | CO(2-(trifluoromethyl)-4-fluorophenyl) | methyl | 502 |
| 200 | 2 | CO(2,4-difluorophenyl) | methyl | 452 |
| 201 | 1 | CO(2-(trifluoromethyl)-4-fluorophenyl) | n-propyl | 516 |
| 202 | 2 | SO$_2$(2-chloro-4-fluorophenyl) | H | 490 |
| 203 | 2 | SO$_2$(2,4-difluorophenyl) | H | 474 |
| 204 | 1 | SO$_2$(3-chlorophenyl) | methyl | 472 |
| 205 | 1 | SO$_2$(2-chloro-4-fluorophenyl) | methyl | 490 |
| 206 | 1 | SO$_2$(3-chlorophenyl) | n-propyl | 500 |
| 207 | 2 | CO(2,4-difluorophenyl) | n-propyl | 480 |
| 208 | 2 | CO(2-chloro-4-fluorophenyl) | n-propyl | 496 |
| 209 | 2 | CO(2-(trifluoromethyl)-4-fluorophenyl) | n-propyl | 530 |

Example 210

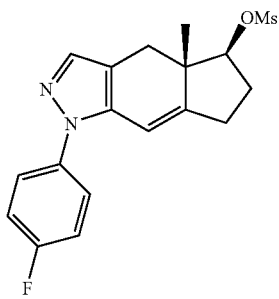

COMPOUND A (300 mg, 1.06 mmol) was diluted into methanol (10 mL) and treated with sodium borohydride (40 mg, 1.06 mmol). The mixture was maintained at 23° C. for 1.5 h, then partitioned between $NH_4Cl_{(aq)}$ and methylene chloride, the organic phase dried over anhydrous sodium sulfate, and concentrated in vacuo. This alcohol intermediate (130 mg, 0.46 mmol) was diluted into $CH_2Cl_2$ (5 mL), cooled to −20° C., treated with $Et_3N$ (0.092 mL, 0.64 mmol) and then methanesulfonyl chloride (0.042 mL, 0.55 mmol). The mixture was stirred at -20° C. for 10 min, warmed to 23° C. and maintained for 1 h. The mixture was then quickly partitioned between cold $NH_4Cl_{(aq)}$ and methylene chloride, the organic phase dried over anhydrous sodium sulfate, and concentrated in vacuo. The crude product mesylate was of sufficient purity to be used in subsequent reactions and was characterized by $^1H$ NMR, HPLC and mass spectrometry (m/z: 363 ($M^+$+1)).

Example 211

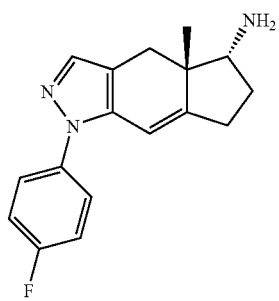

EXAMPLE 210 (64 mg, 0.177 mmol) was diluted into dimethyl acetamide (18 mL) and treated with sodium azide (530 mg, 8.16 mmol) followed by water (0.20 mL). The mixture was heated in a re-sealable pressure tube at 90° C. for 14 h, cooled to 23° C., then partitioned between water and diethyl ether, the organic phase dried over anhydrous sodium sulfate, and concentrated in vacuo (DMAC remains). The crude product was purified by preparative reverse phase HPLC (C18 $SiO_2$, 0-100% acetonitrile gradient in water with 0.1% TFA eluent). The product azide intermediate (100 mg, 0.324 mmol) was diluted into ethyl acetate (4 mL) and treated with catalytic 10% Pd—C. The system was fitted with a balloon of hydrogen gas, and the mixture stirred under an atmosphere of $H_2$ at 25° C. for 30 min. The mixture was then filtered over celite, washed with EtOAc, and the filtrate concentrated in vacuo to provide the pure amine product which as characterized by $^1H$ NMR, HPLC and mass spectrometry (m/z: 284 ($M^+$+1)).

Examples 212-233

The following epimerized compounds were prepared under conditions similar to those described in the examples above and illustrated in Schemes 4-6. The following examples were characterized by $^1H$ NMR, HPLC and mass spectrometry.

| EX. | $R^v$ Group | $R^{vi}$ Group | MS (m/z) ($M^+$ + 1) |
|---|---|---|---|
| 212 | CO(phenyl) | H | 388 |
| 213 | $SO_2$(2-chloro-4-fluorophenyl) | H | 476 |
| 214 | CO(2-chlorophenyl) | H | 422 |
| 215 | CO(3-chlorophenyl) | H | 422 |
| 216 | CO(2-(trifluoromethyl)phenyl) | H | 456 |
| 217 | CO(isopropyl) | H | 354 |
| 218 | CO(tert-butyl) | H | 368 |
| 219 | CO(3-thiopheneyl) | H | 394 |
| 220 | CO(2-thiopheneyl) | H | 394 |
| 221 | CO(2,4,5-trifluorophenyl) | H | 442 |
| 222 | CO(2,5-difluorophenyl) | H | 424 |
| 223 | $CO_2$(phenyl) | H | 404 |
| 224 | $SO_2$(phenyl) | H | 424 |
| 225 | CO(2-chlorophenyl) | methyl | 436 |
| 226 | CO(2-(trifluoromethyl)phenyl) | methyl | 470 |
| 227 | CO(3-chlorophenyl) | methyl | 436 |
| 228 | CONH(phenyl) | H | 403 |
| 229 | CO(2,6-difluorophenyl) | H | 424 |
| 230 | $COCH_2$(2,4-difluorophenyl) | H | 438 |
| 231 | CO(2,4-difluorophenyl) | H | 424 |
| 232 | CO(2-fluorophenyl) | H | 406 |
| 233 | CO(2-(trifluoromethyl)-4-fluorophenyl) | n-propyl | 516 |

Example 234

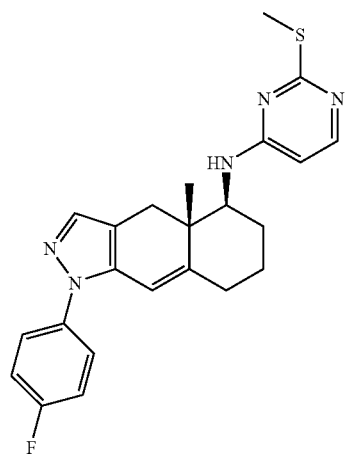

Using the procedure for the synthesis of EXAMPLE 128, COMPOUND B was transformed into the primary amine as shown in Scheme 7. This amine (20 mg, 0.067 mmol) was then combined with 4-chloro-2-methylthiopyrimidine (0.008 mL, 0.067 mmol), K$_3$PO$_4$ (286 mg, 1.35 mmol) and diluted into degassed toluene (0.7 mL) under an argon atmosphere. To this was added tris(dibenzylideneacetone)-dipalladium(0) (6 mg, 0.007 mmol) and (diphenylphosphino)ferrocene (7 mg, 0.014 mmol) and the resulting reaction mixture was heated to 100° C. for 15 hours. Upon cooling, the reaction mixture was filtered through celite, washed with methylene chloride and evaporated under reduced pressure. The crude product was purified by preparative thin layer chromatography (1000 micron SiO$_2$, 20×20 cm, 50% EtOAc-hexane) to provide the product which was characterized by $^1$H NMR, HPLC and mass spectrometry (m/z: 422 (M$^+$+1)).

Examples 235-250

The following compounds were prepared under conditions similar to those described in the examples above and illustrated in Scheme 7. Installation of an R$^{vii}$ Group (other than hydrogen shown in the table below) was accomplished using conditions described in EXAMPLES 96-125. The following examples were characterized by $^1$H NMR, HPLC and mass spectrometry.

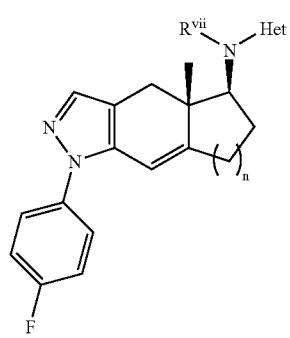

| EX. | n | Het (Heterocycle) | R$^{vii}$ Group | MS (m/z) (M$^+$ + 1) |
|---|---|---|---|---|
| 235 | 1 | 2-pyridyl | H | 361 |
| 236 | 1 | 4-isoquinolyl | H | 411 |
| 237 | 1 | 2-(4-methyl)pyridyl | H | 375 |
| 238 | 1 | 5-pyrimidyl | H | 362 |
| 239 | 1 | 3-pyridyl | H | 361 |
| 240 | 1 | 2-pyrimidyl | H | 362 |
| 241 | 1 | 2-pyrimidyl | methyl | 376 |
| 242 | 1 | 2-pyrimidyl | n-propyl | 404 |
| 243 | 1 | 4-(2-methylthio)pyrimidyl | H | 408 |
| 244 | 2 | 4-(2-methylthio)pyrimidyl | methyl | 436 |
| 245 | 2 | 4-(2-methylthio)pyrimidyl | n-propyl | 464 |
| 246 | 1 | 2-(4-trifluoromethyl)pyridyl | H | 429 |
| 247 | 2 | 2-(4-trifluoromethyl)pyridyl | H | 443 |
| 248 | 1 | 2-pyrazinyl | H | 362 |
| 249 | 1 | 4-(2,3,5,6-tetrafluoro)pyridyl | H | 433 |
| 250 | 2 | 4-(2,3,5,6-tetrafluoro)pyridyl | H | 447 |

Example 251

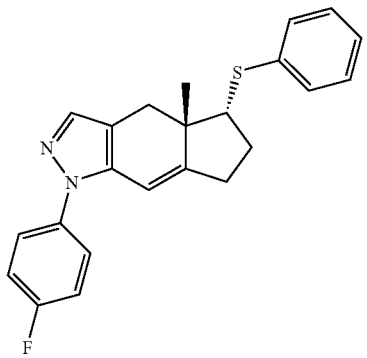

Cesium carbonate (46 mg, 0.141 mmol) was diluted into dry DMF (0.7 mL) and the solution was treated with benzene thiol (0.014 mL, 0.141 mmol). The reaction mixture was stirred at 23° C. for 20 min and then treated with a solution of EXAMPLE 210 (17 mg, 0.047 mmol) in dry DMF (0.8 mL). The reaction mixture was then heated at 70° C. for 16 h, cooled to 23° C., partitioned between EtOAc and NaHCO$_3$ $_{(aq)}$, the organic phase washed excessively with water to remove DMF, the organic phase dried over anhydrous sodium sulfate and concentrated in vacuo. The residue was purified by preparative reverse phase HPLC (C18 SiO$_2$, 0-100% acetonitrile gradient in water with 0.1% TFA eluent) to provide the product which was characterized by $^1$H NMR, HPLC and mass spectrometry (m/z: 377 (M$^+$+1)).

Example 252

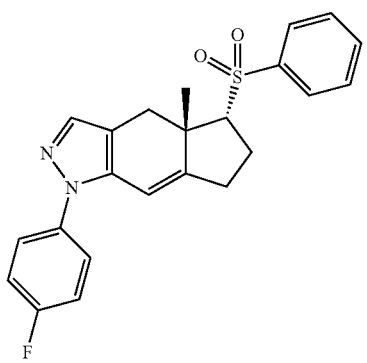

Example 251 (4 mg, 0.011 mmol) was dissolved in methanol (0.4 mL), treated with a solution of oxone (14 mg, 0.022 mmol) in water (0.20 mL), and the reaction mixture vigorously stirred at 23° C. for 1.5 h. The methanol was removed under reduced pressure, and the remaining aqueous was extracted with methylene chloride. The organic phase was then dried over anhydrous sodium sulfate, and concentrated in vacuo to provide the pure product which was characterized by $^1$H NMR, HPLC and mass spectrometry (m/z: 409 (M$^+$+1)).

Examples 253-257

The following compounds were prepared under conditions similar to those described in the examples above and illustrated in Scheme 8. The following examples were characterized by ¹H NMR, HPLC and mass spectrometry.

| EXAMPLE | Ar Group | MS (m/z) (M⁺ + 1) |
|---|---|---|
| 253 | 2-chlorophenyl | 411 |
| 254 | 3-chlorophenyl | 411 |
| 255 | 2-(trifluoromethyl)phenyl | 445 |
| 256 | 2,6-dichlorophenyl | 445 |
| 257 | 2,4-dichlorophenyl | 445 |

BIOLOGICAL ASSAYS

The activity of the compounds of the present invention regarding glucocorticoid receptor affinity can be evaluated using the following human GR binding assay:

GR Ligand Binding Assay

For the hGRI ligand binding assay, cytosols were prepared from recombinant baculovirus expressed receptors. Frozen cell pellets were dounce homogenized in ice cold KPO₄ buffer (10 mM KPO₄, 20 mM sodium molybdate, 1 mM EDTA, 5 mM DTT and complete protease inhibitor tablets from Boehringer Mannheim) with a "B" plunger. The homogenates were centrifuged at 35,000×g for 1 h at 4° C. in a JA-20 rotor. The $IC_{50}$s were determined by incubating the cytosols at a final concentration of 2.5 nM [1,2,4,6,7-³H] Dexamethasone in the presence of increasing concentrations (10-11 to 10-6) of cold dexamethasone or the ligands at 4° C. for 24 h. Bound and free were separated by a gel filtration assay, (Geissler et al, personal communication). Half of the reaction was added to a gel filtration plate (MILLIPORE) containing SEPHADEX® G-25 beads that was previously equilibrated with KPO4 buffer containing 1 mg/ml BSA and centrifuged at 1000×g for 5 min. The reaction plate was centrifuged at 1000×g for 5 min. and the reactions were collected in a second 96-well plate and scintillation cocktail was added and counted in (Wallac) double coincidence beta counter. The $IC_{50}$ values were calculated using a 4-parameter fit program. The compounds of this invention demonstrated a range of GR affinity in the above assay with $IC_{50}$ values between 10 uM and 1 nM.

What is claimed is:

1. A compound of Formula II:

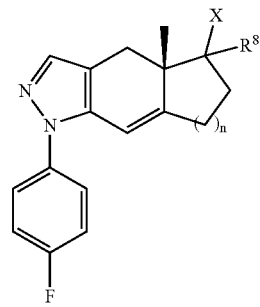

or a pharmaceutically acceptable salt or hydrate thereof, wherein:

X is selected from the group consisting of: —OR$^a$, —N(R$^b$)—Y—R$^c$, —S(O)$_j$-R$^d$, wherein:

Y is selected from a bond, —C(O)—, —C(O)—O—, wherein the point of attachment of the "—O—" group is to R$^c$ forming an alkoxy moiety, —S(O)₂— and —C(O)—N(R¹²)—, wherein the point of attachment of the nitrogen group is to R$^c$, and j is 0, 1 or 2, n is 1, R$^a$, R$^b$, R$^c$, R$^d$ and R⁸ are each independently selected from the group consisting of:

(1) hydrogen, except that R$^d$ is not hydrogen and R$^c$ is hydrogen only when Y is a bond or —C(O)—N (R¹²)—,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) HET¹,
(9) —$C_{1-6}$alkyl-HET²,
(10) aralkenyl,
(11) aralkynyl and
(12) arylsulfonylalkyl, wherein items (2) to (5) above and the alkyl portions of items (7), (9) and (12) above and the alkenyl portion of item (10) above and the alkynyl portion of item (11) above are optionally substituted with oxo and optionally substituted with one to three substituents independently selected from the group consisting of: halo, OR¹¹, N(R¹²)₂, $C_{3-6}$cycloalkyl and $C_{1-4}$alkyl-S(O)$_m$—, wherein m is 0, 1 or 2, and wherein items (6) and (8) above and the aryl portion of items (7), (10), (11) and (12) above and the HET² portion of item (9) above are optionally substituted with one to five substituents independently selected from the group consisting of:

(a) halo,
(b) OR¹¹,
(c) N(R¹²)₂,
(d) $C_{1-6}$alkyl,
(e) $C_{2-6}$alkenyl,
(f) $C_{2-6}$akynyl,
(g) $C_{1-6}$alkyl-S(O)$_p$—, wherein p is 0, 1 or 2,
(h) aryl,
(i) aryl-S(O)$_q$—, wherein q is 0, 1 or 2, (j) HET³,
(k) aralkyl,
(l) aroyl,
(m) aryloxy,
(n) aralkoxy and
(o) CN,
wherein items (d) to (g) above and the alkyl portions of item (k) above are optionally substituted with one to three substituents independently selected from the group consisting of: halo, OR¹¹ and N(R¹²)₂, and
wherein items (h), (i), (j), (l) and (m) above and the aryl portions of items (k) and (n) above are optionally substituted with one to three substituents independently selected from the group consisting of: halo, OR¹² and C₁₋₄alkyl,
each R¹¹ and R¹² is independently selected from the group consisting of hydrogen and C₁₋₄alkyl, optionally substituted with 1 to 3 halo groups; and
HET¹, HET² and HET³ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

2. The compound according to claim 1 wherein
X is —ORᵃ,
and
Rᵃ is selected from the group consisting of:
(1) hydrogen,
(2) acetyl,
(3) benzyl,
(4) C₁₋₆alkyl,
(5) C₂₋₆alkenyl,
(6) C₂₋₆alkynyl and
(7) C₃₋₆cycloalkyl,
R⁸ is selected from the group consisting of:
(1) hydrogen,
(2) C₁₋₆alkyl,
(3) C₂₋₆alkenyl,
(4) C₂₋₆akynyl,
(5) C₃₋₆cycloalkyl,
(6) aryl,
(7) aralkyl,
(8) HET¹,
(9) —C₁₋₆alkyl-HET²,
(10) aralkenyl,
(11) aralkynyl, and
(12) arylsulfonylalkyl
wherein items (2) to (5) above and the alkyl portions of items (7), (9) and (12) above and the alkenyl portion of item (10) above and the alkynyl portion of item (11) above are optionally substituted with oxo and optionally substituted with one to three substituents independently selected from the group consisting of: halo, OR¹¹ and C₃₋₆cycloalkyl,
wherein items (6) and (8) above and aryl portion of items (7), (10), (11) and (12) above and the HET² portion of item (9) above are optionally substituted with one to five substituents independently selected from the group consisting of:
(a) halo,
(b) C₁₋₆alkyl,
(c) C1-4alkoxy and
(d) aryl,
R¹¹ is selected from the group consisting of hydrogen and C₁₋₄alkyl, optionally substituted with 1 to 3 halo groups; and
HET¹ and HET² are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

3. The compound according to claim 2 wherein:
R⁸ is selected from the group consisting of:
(1) hydrogen,
(2) C₁₋₆alkyl,
(3) C₂₋₆alkenyl,
(4) C₂₋₆akynyl,
(5) C₃₋₆cycloalkyl,
(6) phenyl or naphthyl,
(7) benzyl or phenethyl,
(8) benzothiophene,
(9) phenylethenyl,
(10) phenylethynyl, and
(11) phenylsulfonylmethyl,
wherein items (2) to (5) above are optionally substituted with one to three substituents independently selected from the group consisting of: halo, OR¹¹ and C₃₋₆cycloalkyl,
wherein item (6) above and the phenyl portions of items (7), (9), (10) and (11) above are optionally substituted with one to five substituents independently selected from the group consisting of:
(a) halo,
(b) C₁₋₆alkyl,
(c) C₁₋₄alkoxy and
(d) phenyl, 4. The compound according to claim 1 wherein:
X is —N(Rᵇ)—Y—Rᶜ, wherein:

Y is selected from —C(O)—, C(O)O—, wherein the point of attachment of the "—O—" group is to $R^c$ forming an alkoxy moiety, —S(O)$_2$— and —C(O)—N(R$^{12}$)—, wherein the point of attachment of the nitrogen group is to $R^c$, and $R^8$ is hydrogen, $R^b$ and $R^c$ are each independently selected from the group consisting of:
(1) hydrogen, except that $R^c$ is not hydrogen,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) HET$^1$,
(9) —$C_{1-6}$alkyl-HET$^2$,
(10) aralkenyl,
(11) aralkynyl and
(12) arylsulfonylalkyl,
wherein items (2) to (5) above and the alkyl portions of items (7), (9) and (12) above and the alkenyl portion of item (10) above and the alkynyl portion of item (11) above are optionally substituted with oxo and optionally substituted with with one to three substituents independently selected from the group consisting of: halo, OR$^{11}$, N(R$^{12}$)$_2$, $C_{3-6}$cycloalkyl and $C_{1-4}$alkyl-S(O)$_m$—, wherein m is 0, 1 or 2, and
wherein items (6) and (8) above and the aryl portion of items (7), (10), (11) and (12) above and the HET$^2$ portion of item (9) above are optionally substituted with one to five substituents independently selected from the group consisting of:
(a) halo,
(b) OR$^{11}$,
(c) N(R$^{12}$)$_2$,
(d) $C_{1-6}$alkyl,
(e) $C_{2-6}$alkenyl,
(f) $C_{2-6}$akynyl,
(g) $C_{1-6}$alkyl-S(O)$_p$—, wherein p is 0, 1 or 2,
(h) aryl,
(i) aryl-S(O)$_q$—, wherein q is 0, 1 or 2,
(j) HET$^3$,
(k) aralkyl,
(l) aroyl,
(m) aryloxy,
(n) aralkoxy and
(o) CN,
wherein items (d) to (g) above and the alkyl portions of item (k) above are optionally substituted with one to three substituents independently selected from the group consisting of: halo, OR$^{11}$ and N(R$^{12}$)$_2$, and
wherein items (h), (i), (j), (l) and (m) above and the aryl portions of items (k) and (n) above are optionally substituted with one to three substituents independently selected from the group consisting of: halo, OR$^{12}$ and $C_{1-4}$alkyl,
each R$^{11}$ and R$^{12}$ is independently selected from the group consisting of hydrogen and $C_{1-4}$alkyl, optionally substituted with 1 to 3 halo groups; and HET$^1$, HET$^2$ and HET$^3$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

5. The compound according to claim 4 wherein:

$R^b$ and $R^c$ are each independently selected from the group consisting of:
(1) hydrogen, except that $R^c$ is hydrogen only when Y is a bond or —C(O)—N(R$^{12}$)—,
(2) $C_{1-6}$alkyl,
(3) $C_{2-6}$alkenyl,
(4) $C_{2-6}$akynyl,
(5) $C_{3-6}$cycloalkyl,
(6) aryl,
(7) aralkyl,
(8) HET$^1$,
(9) —$C_{1-6}$alkyl-HET$^2$,
(10) aralkenyl, and
(11) aralkynyl,
wherein items (2) to (5) above are optionally substituted with 1-3 halo groups, and
wherein items (6) and (8) and aryl portion of items (7), (10) and (11) above and the HET$^2$ portion of item (9) above are optionally substituted with one to five substituents independently selected from the group consisting of:
(a) halo,
(b) $C_{1-4}$alkyl, optionally substituted with 1-3 halo groups, and
(c) $C_{1-4}$alkylthio, HET$^1$ and HET$^2$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

6. The compound according to claim 5 wherein:

$R^b$ is selected from the group consisting of: hydrogen and $C_{1-4}$alkyl, and R$^c$ is selected from the group consisting of:
(1) C$_{1-4}$alkyl,
(2) phenyl or benzyl, each optionally substituted with 1 to 5 groups independently selected from fluoro, chloro and trifluoromethyl,
(3) naphthyl,
(4) thiopheneyl,
(5) pyridyl,
(6) isoquinolyl,
(7) pyrimidyl and
(8) pyrazyl,
wherein items (4) to (8) above are optionally substitited with 1 to 5 groups independently selected from fluoro, chloro, methyl, methylthio and trifluoromethyl.

7. The compound according to claim 6, wherein R$^c$ is phenyl, optionally substituted with 1 to 5 groups independently selected from fluoro, chloro and trifluoromethyl.

8. The compound according to claim 1, wherein:
X is —S(O)$^j$-R$^d$, wherein j is 0, 1 or 2,
R$^g$ is hydrogen, and
R$^d$ is selected from the group consisting of:
(1) C$_{1-6}$alkyl,
(2) C$_{2-6}$alkenyl,
(3) C$_{2-6}$akynyl,
(4) C$_{3-6}$cycloalkyl,
(5) aryl,
(6) aralkyl,
(7) HET$^1$,
(8) —C$_{1-6}$alkyl-HET$^2$,
(9) aralkenyl, and
(10) aralkynyl,
wherein items (1) to (4) above are optionally substituted with 1-3 halo groups, and
wherein items (5) and (7) and aryl portion of items (6), (9) and (10) above and the HET$^2$ portion of item (8) above are optionally substituted with one to five substituents independently selected from the group consisting of:
(a) halo,
(b) C$_{1-4}$alkyl, optionally substituted with 1-3 halo groups, and
(c) C$_{1-4}$alkylthio, and HET$^1$ and HET$^2$ are each independently selected from the group of heterocycles consisting of: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

9. The compound according to claim 8, wherein
R$^d$ is phenyl, optionally substituted with 1 to 5 groups independently selected from fluoro, chloro and trifluoromethyl.

10. A compound selected from the following group:

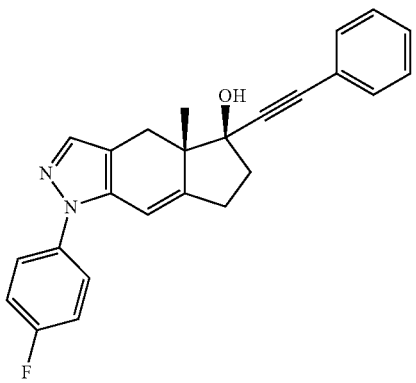

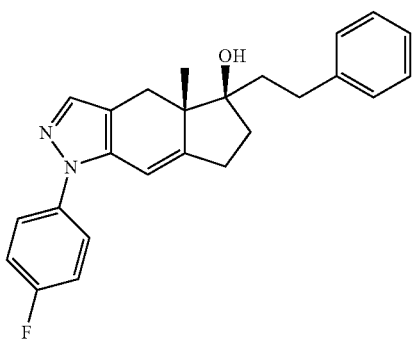

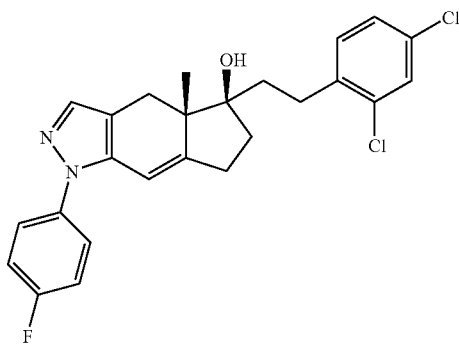

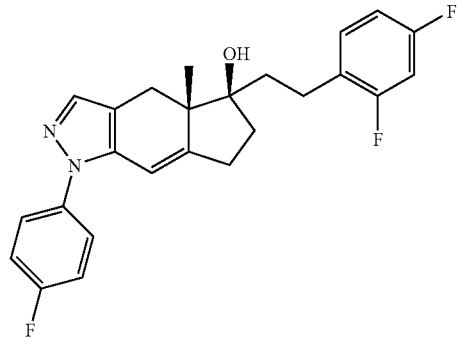

-continued

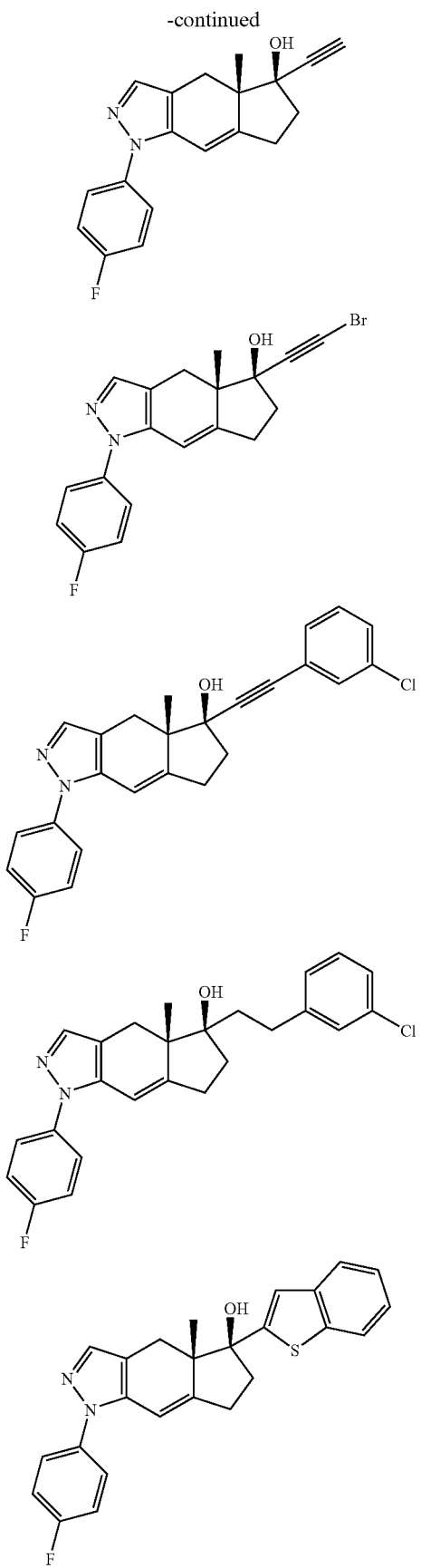

-continued

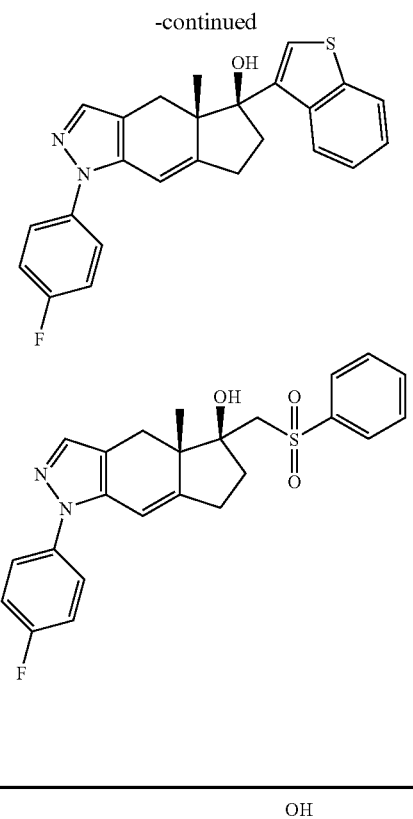

| n | R Group |
|---|---|
| 1 | Vinyl |
| 1 | Allyl |
| 1 | 3-butenyl |
| 1 | n-pentyl |
| 1 | 3-methylbutyl |
| 1 | 2-cyclohexylethyl |
| 1 | 3,3-dimethylbutyl |
| 1 | 4-methyl-3-pentenyl |
| 1 | 4,4,4-trifluorobutyl |
| 1 | 3,4,4-trifluoro-3-butenyl |
| 1 | 3-methoxypropyl |
| 1 | 2-(2-chlorophenyl)ethyl |
| 1 | 2-(4-chlorophenyl)ethyl |
| 1 | 2-(4-fluorophenyl)ethyl |
| 2 | 2-(4-fluorophenyl)ethyl |
| 1 | 2-(2,5-difluorophenyl)ethyl |
| 1 | 2-(2,3-difluorophenyl)ethyl |
| 1 | 2-(3,5-difluorophenyl)ethyl |
| 1 | 2-(4-methoxyphenyl)ethyl |
| 1 | 2-(2-naphthyl)ethyl |
| 1 | 2-(3-(trifluoromethyl)phenyl)ethyl |
| 1 | 2-(2-methoxyphenyl)ethyl |
| 1 | 2-(4-tert-butylphenyl)ethyl |
| 1 | 2-(4-methylphenyl)ethyl |
| 1 | 2-(1-naphthyl)ethyl |
| 1 | 2-(2-methylphenyl)ethyl |
| 1 | 2-(3-methylphenyl)ethyl |

-continued

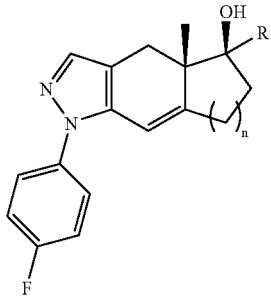

| n | R Group |
|---|---|
| 1 | 2-(2-fluorophenyl)ethyl |
| 1 | 2-(3-fluorophenyl)ethyl |
| 1 | 2-(3,4-dichlorophenyl)ethyl |
| 1 | 2-(2-chloro-4-fluorophenyl)ethyl |
| 1 | 2-(3-thiopheneyl)ethyl |
| 1 | 3-(N-pyrrolyl)propyl |
| 1 | E-2-phenylethenyl |
| 1 | Z-2-phenylethenyl |
| 1 | 2-(2,4-difluorophenyl)ethynyl |
| 1 | 2-(2-thiopheneyl)ethyl |
| 1 | 2-(3,4-difluorophenyl)ethyl |
| 1 | 2-(3,4,5-trifluorophenyl)ethyl |
| 1 | H |

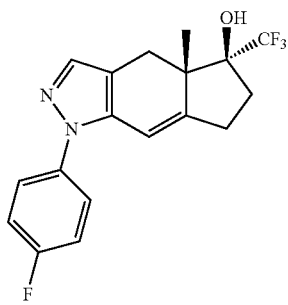

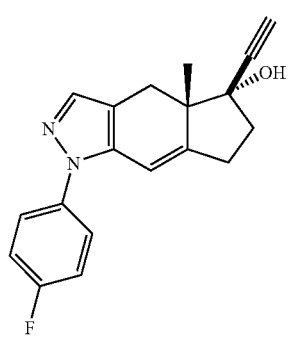

-continued

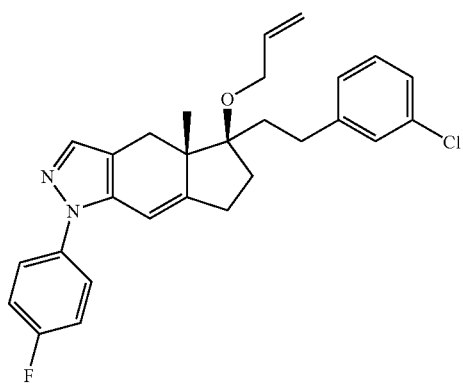

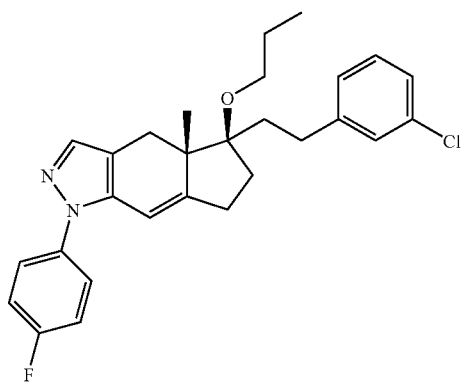

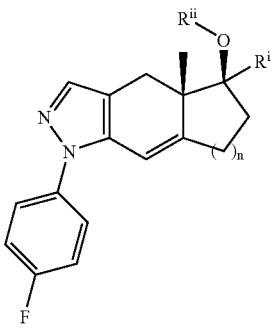

| n | R$^i$ Group | R$^{ii}$ Group |
|---|---|---|
| 1 | H | n-propyl |
| 1 | phenethyl | cyclopropylmethyl |
| 1 | phenethyl | E-2-butenyl |
| 1 | 2-(2,4-dichlorophenyl)ethyl | methyl |
| 1 | 2-(2-chlorophenyl)ethyl | methyl |
| 1 | 2-(3-chlorophenyl)ethyl | methyl |
| 1 | n-pentyl | methyl |
| 1 | 2-(4-fluorophenyl)ethyl | methyl |
| 1 | 2-(2,4-dichlorophenyl)ethyl | benzyl |
| 1 | 2-(2,4-dichlorophenyl)ethyl | allyl |
| 1 | 2-(2,4-dichlorophenyl)ethyl | n-propyl |
| 1 | 2-(2-chlorophenyl)ethyl | n-propyl |
| 1 | phenethyl | n-propyl |
| 1 | phenethyl | methyl |
| 1 | 2-(3-chlorophenyl)ethynyl | allyl |
| 1 | 2-(3-chlorophenyl)ethynyl | n-propyl |
| 1 | 2-(2,4-difluorophenyl)ethyl | methyl |

-continued

| n | R$^i$ Group | R$^{ii}$ Group |
|---|---|---|
| 1 | phenethyl | E-2-pentenyl |
| 1 | trifluoromethyl | allyl |
| 1 | trifluoromethyl | n-propyl |
| 1 | 2-(3-methylphenyl)ethyl | methyl |
| 1 | phenethyl | n-butyl |
| 1 | phenethyl | n-pentyl |
| 1 | 2-(3,4-difluorophenyl)ethyl | n-propyl |
| 1 | 2-(3-fluorophenyl)ethyl | methyl |

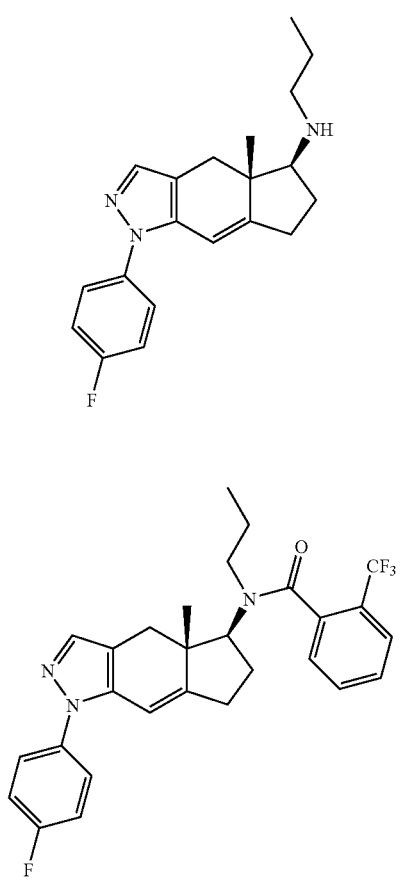

-continued

| n | R$^{iii}$ Group | R$^{iv}$ Group |
|---|---|---|
| 1 | CO(3,3,3-trifluoropropyl) | H |
| 1 | CO(2-(trifluoromethyl)phenyl) | H |
| 1 | CO(3-chlorophenyl) | H |
| 1 | COCH$_2$(2-(trifluoromethyl)phenyl) | H |
| 1 | CO(2,4,5-trifluorophenyl) | H |
| 1 | CO(3-thiopheneyl) | H |
| 1 | COCH$_2$(2,4-difluorophenyl) | H |
| 1 | COCH$_2$(3-chlorophenyl) | H |

-continued

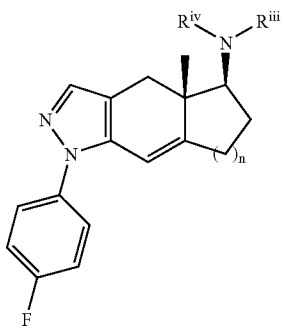

| n | R$^{iii}$ Group | R$^{iv}$ Group |
|---|---|---|
| 1 | CO(3-chloro-4-fluorophenyl) | H |
| 1 | COCH$_2$(2,5-difluorophenyl) | H |
| 1 | COCH$_2$(2-thiopheneyl) | H |
| 1 | COCH$_2$(3-thiopheneyl) | H |
| 1 | CO(2-chloro-5-fluorophenyl) | H |
| 1 | COCH$_2$(3-chloro-4-fluorophenyl) | H |
| 1 | CO(2,4,5-trifluorophenyl) | methyl |
| 1 | CO(2-(trifluoromethyl)phenyl) | methyl |
| 1 | CO(2-thiopheneyl) | methyl |
| 1 | CO(3-chlorophenyl) | methyl |
| 1 | CO(phenyl) | H |
| 1 | CO(2,4-difluorophenyl) | H |
| 1 | COCH$_2$(3-chloro-4-fluorophenyl) | methyl |
| 1 | CO(2,4-difluorophenyl) | methyl |
| 1 | COCH$_2$(2-(trifluoromethyl)phenyl) | methyl |
| 1 | CO(2-fluorophenyl) | H |
| 1 | CO(2,6-difluorophenyl) | H |
| 1 | CO(2-chlorophenyl) | H |
| 1 | CO(1-naphthyl) | H |
| 1 | CO(2-(trifluoromethyl)-4-fluorophenyl) | H |
| 1 | CO(2,5-difluorophenyl) | H |
| 1 | CO(2,3-difluorophenyl) | H |
| 1 | CO(2-chloro-4-fluorophenyl) | H |
| 1 | CO(2-chloro-3-fluorophenyl) | H |
| 1 | CO(tert-butyl) | H |
| 1 | CO(isopropyl) | H |
| 1 | CO(2-chloro-3-fluorophenyl) | methyl |
| 1 | CO(2-(trifluoromethyl)-4-fluorophenyl) | methyl |
| 1 | CO(2,6-difluorophenyl) | methyl |
| 1 | CO(2-chloro-4-fluorophenyl) | methyl |
| 1 | SO$_2$(phenyl) | H |
| 1 | CO(2,6-dichlorophenyl) | methyl |
| 1 | CO(2,6-dichlorophenyl) | H |
| 1 | SO$_2$(2,4-difluorophenyl) | H |
| 1 | CO(2,4-difluorophenyl) | n-propyl |
| 1 | SO$_2$(3-chlorophenyl) | H |
| 2 | CO(3-chlorophenyl) | H |
| 1 | SO$_2$(2-chloro-4-fluorophenyl) | H |
| 1 | CO$_2$(phenyl) | methyl |
| 1 | CO$_2$(phenyl) | H |
| 1 | CONH(phenyl) | H |
| 1 | SO$_2$(2-fluorophenyl) | H |
| 1 | SO$_2$(2-chlorophenyl) | H |
| 1 | CONH(phenyl) | methyl |
| 1 | SO$_2$(2-(trifluoromethyl)phenyl) | H |
| 1 | SO$_2$(3-fluorophenyl) | H |
| 1 | CO(2-chloro-4-fluorophenyl) | n-propyl |
| 1 | CO(2-(trifluoromethyl)-4-fluorophenyl) | n-propyl |
| 1 | SO$_2$(3-chlorophenyl) | methyl |
| 1 | SO$_2$(2-chloro-4-fluorophenyl) | methyl |
| 1 | SO$_2$(3-chlorophenyl) | n-propyl |

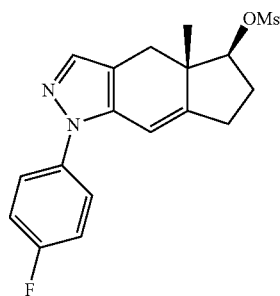

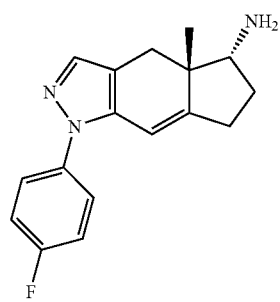

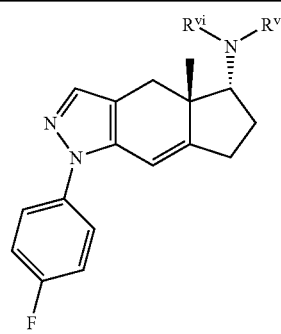

| R$^v$ Group | R$^{vi}$ Group |
|---|---|
| CO(phenyl) | H |
| SO$_2$(2-chloro-4-fluorophenyl) | H |
| CO(2-chlorophenyl) | H |
| CO(3-chlorophenyl) | H |
| CO(2-(trifluoromethyl)phenyl) | H |
| CO(isopropyl) | H |
| CO(tert-butyl) | H |
| CO(3-thiopheneyl) | H |
| CO(2-thiopheneyl) | H |
| CO(2,4,5-trifluorophenyl) | H |
| CO(2,5-difluorophenyl) | H |
| CO$_2$(phenyl) | H |
| SO$_2$(phenyl) | H |
| CO(2-chlorophenyl) | methyl |
| CO(2-(trifluoromethyl)phenyl) | methyl |
| CO(3-chlorophenyl) | methyl |
| CONH(phenyl) | H |
| CO(2,6-difluorophenyl) | H |
| COCH$_2$(2,4-difluorophenyl) | H |
| CO(2,4-difluorophenyl) | H |
| CO(2-fluorophenyl) | H |
| CO(2-(trifluoromethyl)-4-fluorophenyl) | n-propyl |

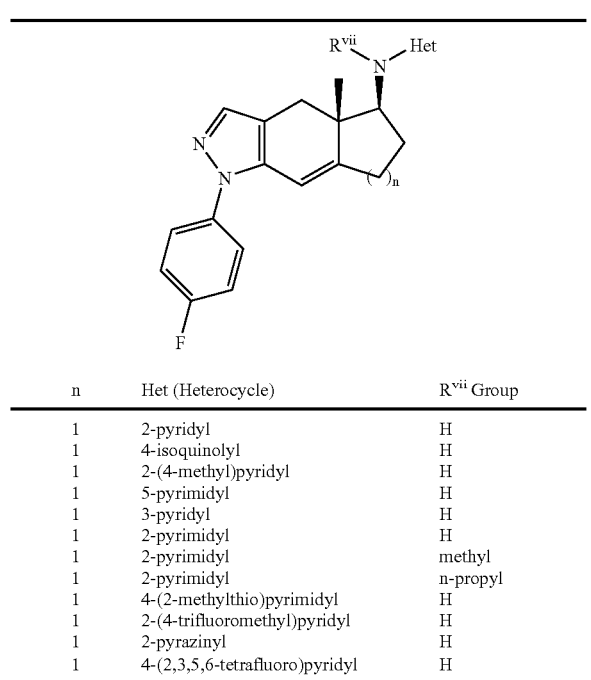

| n | Het (Heterocycle) | R^vii Group |
|---|---|---|
| 1 | 2-pyridyl | H |
| 1 | 4-isoquinolyl | H |
| 1 | 2-(4-methyl)pyridyl | H |
| 1 | 5-pyrimidyl | H |
| 1 | 3-pyridyl | H |
| 1 | 2-pyrimidyl | H |
| 1 | 2-pyrimidyl | methyl |
| 1 | 2-pyrimidyl | n-propyl |
| 1 | 4-(2-methylthio)pyrimidyl | H |
| 1 | 2-(4-trifluoromethyl)pyridyl | H |
| 1 | 2-pyrazinyl | H |
| 1 | 4-(2,3,5,6-tetrafluoro)pyridyl | H |

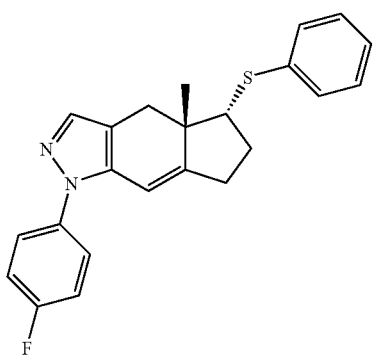

-continued

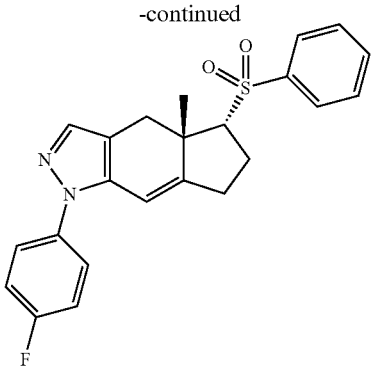

| Ar Group |
|---|
| 2-chlorophenyl |
| 3-chlorophenyl |
| 2-(trifluoromethyl)phenyl |
| 2,6-dichlorophenyl |
| 2,4-dichlorophenyl | or a pharmaceutically acceptable salt of any compound selected from any of the tables above.

11. A pharmaceutical composition comprising a compound according to claim 1 in combination with a pharmaceutically acceptable carrier.

* * * * *